(12) United States Patent
Farr et al.

(10) Patent No.: US 7,749,233 B2
(45) Date of Patent: Jul. 6, 2010

(54) SLEEVE ASSEMBLY FOR SPINAL STABILIZATION SYSTEM AND METHODS OF USE

(75) Inventors: Morteza M. Farr, Tracy, CA (US); Ciaran Keane, San Carlos, CA (US)

(73) Assignee: Innovative Spine, LLC, Madera, CA (US)

( * ) Notice: Subject to any disclaimer, the term of this patent is extended or adjusted under 35 U.S.C. 154(b) by 628 days.

(21) Appl. No.: 11/176,889

(22) Filed: Jul. 6, 2005

(65) Prior Publication Data

US 2006/0293693 A1 Dec. 28, 2006

Related U.S. Application Data

(60) Provisional application No. 60/688,859, filed on Jun. 8, 2005.

(51) Int. Cl.
*A61B 17/58* (2006.01)
*A61B 17/60* (2006.01)
*A61F 2/00* (2006.01)

(52) U.S. Cl. ............... 606/104; 606/86 A; 606/916

(58) Field of Classification Search ............ 606/61, 606/86, 99, 104, 246, 251–279, 86 R, 86 A, 606/916
See application file for complete search history.

(56) References Cited

U.S. PATENT DOCUMENTS

| | | | |
|---|---|---|---|
| 4,805,602 A | 2/1989 | Puno et al. | |
| 5,466,237 A | 11/1995 | Byrd, III et al. | |
| 5,474,555 A | 12/1995 | Puno et al. | |
| 6,929,606 B2 * | 8/2005 | Ritland | 600/201 |
| 7,250,052 B2 * | 7/2007 | Landry et al. | 606/61 |
| 2004/0138662 A1 | 7/2004 | Landry et al. | |
| 2005/0065517 A1 * | 3/2005 | Chin | 606/61 |
| 2005/0085813 A1 * | 4/2005 | Spitler et al. | 606/61 |

(Continued)

OTHER PUBLICATIONS

Stryker Spine, Xia Spinal System Operative Technique, Pamphlet, Sep. 2002.

(Continued)

*Primary Examiner*—Thomas C Barrett
*Assistant Examiner*—Andrew Yang
(74) *Attorney, Agent, or Firm*—GSS Law Group

(57) ABSTRACT

The present invention is a one or two-part sleeve assembly for use during minimally invasive spinal stabilization surgery. An outer sleeve is designed to slide over the coupling between a polyaxial screw and an inner sleeve so as to prevent the screw from becoming disengaged from the inner sleeve during surgery. The outer sleeve includes a lower generally cylindrical wall having a slot, and an upper extension having an outwardly protruding manipulation handle attached to it. The slot in the lower section extends the entire length of the cylindrical wall, giving it a generally "C" shaped cross section. This slot corresponds with a similar slot on the inner sleeve for receiving a stabilizing rod to be attached to the polyaxial screw during surgery. The interior diameter of the lower section is approximately the same as the outer diameter of the inner sleeve, so that the outer sleeve may slide snugly over the inner sleeve and the screw coupling. In addition, the edges of the cylindrical wall adjacent to the longitudinal slot are flattened so as to conform to the shape of the inner sleeve and the head portion of the polyaxial screw where it couples with the inner sleeve.

22 Claims, 18 Drawing Sheets

U.S. PATENT DOCUMENTS

2005/0131408 A1* 6/2005 Sicvol et al. ............... 606/61
2005/0154389 A1* 7/2005 Selover et al. ............. 606/61
2006/0184178 A1* 8/2006 Jackson ..................... 606/99
2006/0247630 A1* 11/2006 Iott et al. ................... 606/61

OTHER PUBLICATIONS

Spinal Concepts, Pathfinder Minimally Invasive Spinal Fixation System Surgical Technique, Pamphlet, Feb. 2004.

* cited by examiner

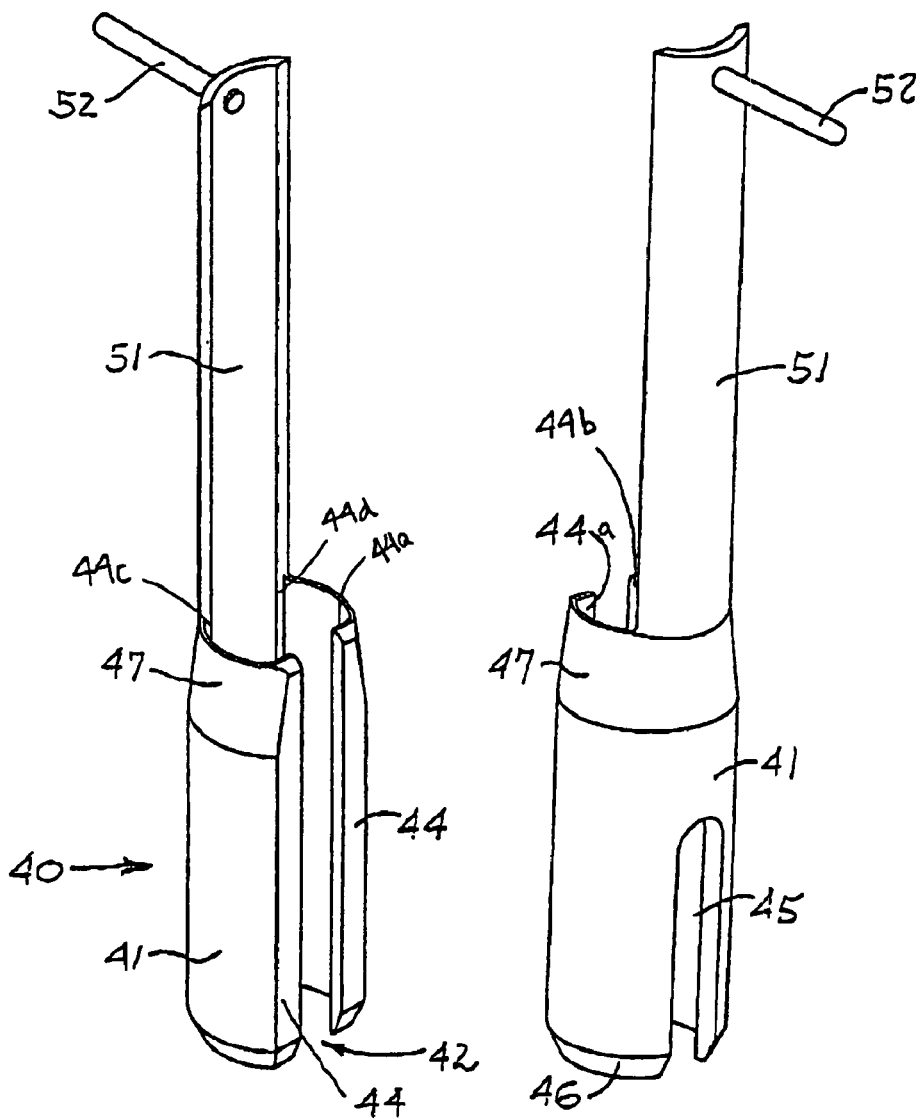
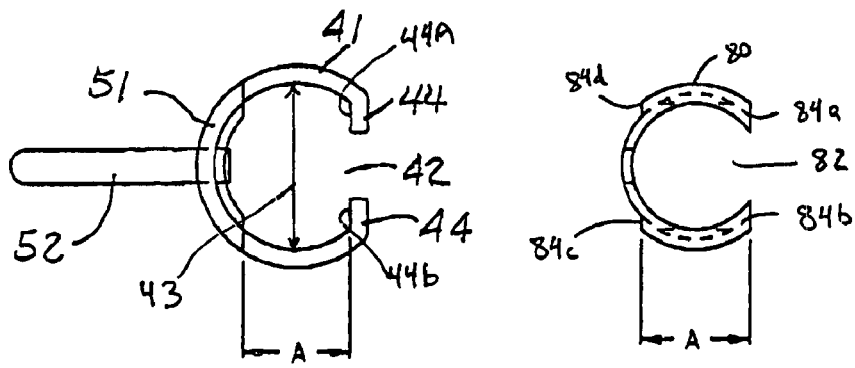
FIG. 15     FIG. 16
FIG. 17     FIG. 17A

SLEEVE ASSEMBLY FOR SPINAL STABILIZATION SYSTEM AND METHODS OF USE

This application claims the benefit of U.S. Provisional Application No. 60/688,859, filed on Jun. 8, 2005, which is incorporated herein by this reference.

BACKGROUND OF THE INVENTION

1. Field of the Invention

The present invention relates to minimally invasive spinal stabilization systems, more particularly to a new and improved inner and outer sleeve assembly used to simplify and expedite minimally invasive spinal stabilization surgery.

2. Description of the Prior Art

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

Spinal stabilization may involve accessing a portion of the spine through soft tissue. Conventional stabilization systems may require a large incision and/or multiple incisions in the soft tissue to provide access to a portion of the spine to be stabilized. Conventional procedures may result in trauma to the soft tissue, for example, due to muscle stripping.

Spinal stabilization systems for a lumbar region of the spine may be inserted during a spinal stabilization procedure using a posterior spinal approach. Conventional systems and methods for posterolateral spinal fusion may involve dissecting and retracting soft tissue proximate the surgical site. Dissection and retraction of soft tissue may cause trauma to the soft tissue, and extend recovery time. Minimally invasive procedures and systems may reduce recovery time as well as trauma to the soft tissue surrounding a stabilization site.

A spinal stabilization system may be installed in a patient to stabilize a portion of a spine. A spinal stabilization system may be installed using a minimally invasive procedure. An instrumentation kit may provide instruments and spinal stabilization system components necessary for forming a spinal stabilization system in a patient.

U.S. Patent Publication No. 2004/0138662 to Landry et al. (hereinafter "Landry"), describes minimally invasive techniques for spinal stabilization. Landry discloses the attachment of a polyaxial screw or bone fastener assembly to a vertebra during minimally invasive surgery. During surgery, the polyaxial screw of Landry is secured to one end of a slotted sleeve using a pair of smaller screws that extend the length of the sleeve. The smaller securing screws are engaged using a driver inserted at the proximal end of the sleeve to accomplish securing the distal end of the sleeve to the polyaxial screw. This attachment prevents the sleeve from becoming disconnected from the polyaxial screw during surgery. Should the sleeve and polyaxial screw become uncoupled during surgery, it would then become necessary to make large incisions to reach the screw to complete the operation such that the surgery is no longer minimally invasive. When the surgery is complete, the smaller screws are undone, and the sleeve is detached from the polyaxial screw and removed. The Landry device and its use are cumbersome in that Landry requires a separate screw in the sleeve as well as a separate driver for engaging and disengaging this screw. The smaller securing screws used in the Landry device are delicate and prone to breakage. Retrieval of broken securing screws is both time consuming and potentially injurious to the patient.

It is therefore desirable to have a simple apparatus and method for securing the engagement of the polyaxial screw during surgery.

SUMMARY OF THE INVENTION

The present invention is a novel inner and outer sleeve assembly for use during minimally invasive spinal stabilization surgery. The outer sleeve of the present invention is designed to slide over the coupling between a polyaxial screw and an inner sleeve so as to prevent the screw from becoming disengaged from the inner sleeve during surgery. The outer sleeve includes a lower generally cylindrical slotted section, and an upper extension attached to the slotted section. The upper extension includes an outwardly protruding handle to assist installation and removal of the outer sleeve. The lower section has a longitudinal slot or opening extending the entire length of the cylindrical wall across from where the extension is attached, giving the lower section a generally "C" shaped cross section. This longitudinal slot corresponds with a similar slot on the inner sleeve for receiving a stabilizing rod to be attached to the polyaxial screw during surgery. The interior diameter of the lower section is approximately the same as the outer diameter of the inner sleeve, so that the outer sleeve may slide snugly over the inner sleeve and the screw coupling. In addition, the edges of the cylindrical wall adjacent to the longitudinal slot are flattened so as to conform to the shape of the upper head portion of the polyaxial screw where it couples with the inner sleeve.

The inner sleeve has register keys that engage the slotted bone screw collar to stop the bone screw collar from rotating. The inner sleeve also has four register flats running its length and a radial wall joining the rear facing register flats only. This permits the outer sleeve to be oriented one way only, slid down fully over the inner tube and bone screw assembly, engaging and locking the bone screw-flats and forgoes the need and inhibits the rotation of the bone screw. As a result, the outer sleeve can only slide over the coupling if it is in a proper orientation according to the mating of the register keys of the inner sleeve and the corresponding register flats of the outer sleeve. This assures both a snug fit over the coupling to prevent the polyaxial screw from becoming detached from the inner sleeve during surgery, and also assures that the slots of the inner and outer sleeve are properly aligned for receiving a stabilization rod.

The cylindrical wall of the lower slotted section may be provided with tapered and/or beveled leading and/or trailing edges to facilitate easy movement of the sleeve through body tissue as it slides around the inner sleeve and coupling. The lower section may be provided with a second longitudinal opening in the form of a partial slot directly across from the first full slot (double slotted embodiment), the second slot allowing a reinforcing rod to pass through the sleeve, extending out from the sleeve in opposite directions for attachment to adjacent polyaxial screws during surgery. The upper extension and the handle thereon may be of any suitable length to allow for the easy installation and removal of the outer sleeve.

In use, once the polyaxial screw has been attached to the inner sleeve, the outer sleeve slides over the inner sleeve and is properly oriented to fit over the coupling between the inner sleeve and the screw. The upper extension and handle are used to facilitate the sliding movements of the outer sleeve over the inner sleeve. This engagement of the outer sleeve to the inner sleeve provides a simple means of preventing the inner sleeve from becoming detached from the polyaxial screw, without the use of complicated and cumbersome inner sleeve configurations and screw drivers. The basic orientation of the slots and subsequently the stabilizing bar can be indicated by "line of sight" alignment of the thin handle and the visible slot opening while employing the bone screw driver or thumb and index finger pressure directly on the inner and outer sleeve assemblage. Fine adjustment will be tuned automatically by the stabilizing bar, proper, or by leveraging it gently in the slot as the bar is fed down the slot. This happens prior to locking the polyaxial screw head.

The mating of the register keys of the inner sleeve and the corresponding register flats of the outer sleeve ensures the alignment of the slots on the inner and outer sleeves for receiving a reinforcing rod during surgery. If the reinforcing rod is to extend out in two directions from the polyaxial screw, then the double slotted embodiment of the invention should be employed. Among other things, during surgery a reinforcing rod is attached to the screw, and extended through the aligned slots for attachment to one or more adjacent screws. When the surgery is complete, and the inner sleeve is to be detached from the polyaxial screw, the outer sleeve is removed from the inner sleeve to allow this detachment to take place. Once the outer sleeve is removed from the inner sleeve, a detachment tool is used to momentarily expand the legs of the inner sleeve so as to disengage the register keys of the inner sleeve legs from the bone screw collar allowing the simple retraction of the inner sleeve and the tool at the same time.

The present invention is designed for use with spinal stabilization systems that include at least one polyaxial fastener coupled to an inner sleeve during surgery. Embodiments of the invention relate the tools used during a minimally invasive surgical spinal stabilization procedure. Embodiments of the invention also include methods for performing minimally invasive spinal stabilization procedures using a unique slotted outer sleeve.

Spinal stabilization systems are often used to achieve rigid pedicle fixation while minimizing the amount of damage to surrounding tissue. A typical spinal stabilization system includes two or more bone screws and a rod member attached to and between them. The bone screws are typically in the form of a polyaxial screw having a movable head. The screw portion is attached to a vertebra, and the head is used for several purposes. During the minimally invasive surgery, the head is coupled to an elongated sleeve for manipulation. It is undesirable for the head to become detached from this sleeve during surgery, as this would require extensive additional surgery to accomplish the same manipulation. The head also receives the elongated member, as well as a device for fastening the elongated member to the head.

Different instruments may be used to form a spinal stabilization system in a patient using a minimally invasive procedure. The instruments may include, but are not limited to, positioning needles, guide wires, sleeves, bone screws driver, mallets, tissue wedges, tissue retractors, tissue dilators, bone awls, taps, and an elongated member length estimator. An instrumentation kit may include, but is not limited to, two or more detachable members (e.g., sleeves), a tissue wedge, an elongated member positioner, a counter torque wrench, an estimating tool, a seater, closure member driver, and/or combinations thereof.

Sleeve assemblies may be used during installation of vertebral level stabilization systems at each of the two vertebrae to be stabilized. It is typical for an interior sleeve assembly to be coupled to the head of a polyaxial screw. The exterior sleeve of the present invention is then slidably attached to the interior sleeve of the sleeve assembly to prevent uncoupling of the interior sleeve and the screw head.

The scale of the measuring device will have a bone screw center-to-center distance given in its simplest form but readily provides the basis for more complete data needed to size any stabilizer bar. This data or additional tables can be inscribed on a scale, in a chart, or programmed in a device such as a calculator, PDA, or personal computer.

A typical method for inserting a stabilization system in a spine involves determining one or more vertebrae of the spine to be targeted for stabilization, making an incision in the skin, inserting a spinal stabilization system, and closing the incision in the skin. This may involve taking images of a patient to assist in determining target locations for insertion of the assemblies in vertebrae to be stabilized. Markings are made on the patient to indicate the target locations, and incisions are made in the patient's skin between the target locations. A targeting needle is then inserted into a first pedicle. Imaging may be used to monitor orientation and depth of the targeting needle during insertion.

After insertion of the targeting needle, a guide wire is generally inserted through a hollow shaft of the targeting needle into a first pedicle. The targeting needle may then be removed from the patient. A bone screw assembly is then coupled to an inner sleeve member having longitudinal slots therein, and inserted into the first pedicle. The outer sleeve of the present invention slides over the inner sleeve and coupling to prevent detachment, the slots of the sleeves being aligned to receive a stabilizing rod. This procedure is repeated for a second pedicle, and potentially additional pedicles. One or more stabilizing rods are then guided down the slots in the sleeves and attached to and between the bone screws. When the attachment of the rod(s) is completed, the outer sleeves may be removed, and the inner sleeves detached from the bone screws. The incision in the skin may be closed.

It is therefore a primary object of the present invention to provide a surgical tool for use in a minimally invasive spinal stabilization procedure that maintains the coupling between a bone screw and an inner sleeve attached thereto during surgery.

It is also an important object of the present invention to provide simplified methods for maintaining the coupling between a bone screw and an inner sleeve attached thereto during minimally invasive spinal stabilization surgery.

It is a further important object of the present invention to provide an inner and outer sleeve for use in maintaining the coupling between a bone screw and the inner sleeve attached thereto during minimally invasive spinal stabilization surgery that includes a longitudinal slot corresponding to a similar slot in the inner sleeve that allows both sleeves to receive a stabilization rod that is ultimately attached to the bone screw.

It is a further important object of the present invention to provide an inner and outer sleeve for use in maintaining the coupling between a bone screw and the inner sleeve attached thereto during minimally invasive spinal stabilization surgery having an extension and handle that allows the outer sleeve of the invention to be easily manipulated during surgery.

Additional objects of the invention will be apparent from the detailed descriptions and the claims herein.

BRIEF DESCRIPTION OF THE DRAWINGS

FIG. 15 is a front perspective view of an embodiment of the outer sleeve of the present invention.

FIG. 16 is a rear perspective view of an embodiment of the outer sleeve of the present invention.

FIG. 17 is a top view of an embodiment of the outer sleeve of the present invention.

FIG. 17A is a top view of the inner sleeve of the present invention.

DETAILED DESCRIPTION

Spinal stabilization systems are installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. More and more frequently, spinal stabilization systems are installed using a minimally invasive procedure. A special instrumentation set is used for such procedures which include surgical instruments as well as the components used to form the spinal stabilization system in the patient.

Spinal stabilization systems are frequently used to achieve rigid pedicle fixation while minimizing the amount of damage to surrounding tissue. In some embodiments, a spinal stabilization system may be used to provide stability to two adjacent vertebrae (i.e., one vertebral level), and may include two bone screw assemblies. In such situations, a bone screw assembly is attached to each of the vertebrae to be stabilized. An elongated member in the form of a stabilization rod is the attached to the two bone screws assemblies. In other situations, multiple bone screw assemblies may be attached to adjacent vertebrae, and a single stabilization rod is extended between and attached to each of the multiple assemblies.

During surgery, each bone screw is coupled to a slotted sleeve. In order to maintain the minimal invasiveness of the surgery, it is important that the bone screw not become detached from this inner sleeve during surgery. The outer sleeve of the present invention facilitates maintaining this coupling. In addition, the outer sleeve of the present invention is designed so that it fits over the inner sleeve and coupling only when properly oriented. Thus, when properly installed, the present invention assures the surgeon that proper orientation has been achieved, and also identifies what that orientation is during surgery.

Figure 12:
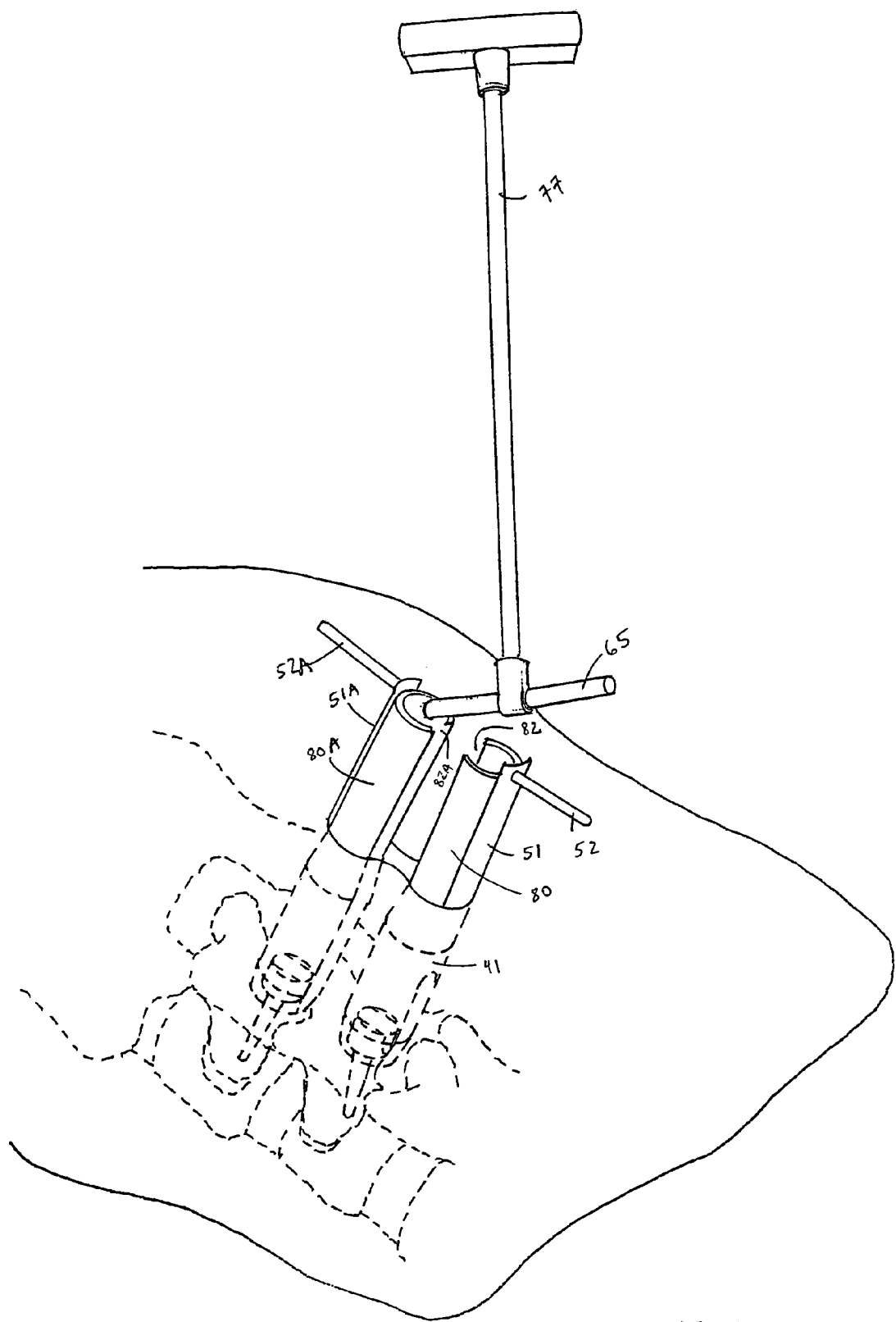
FIG. 12 is a perspective view of the placement of a stabilizing rod member in the aligned slots of the sleeve assemblies during a minimally invasive spinal procedure.
Figure 13:
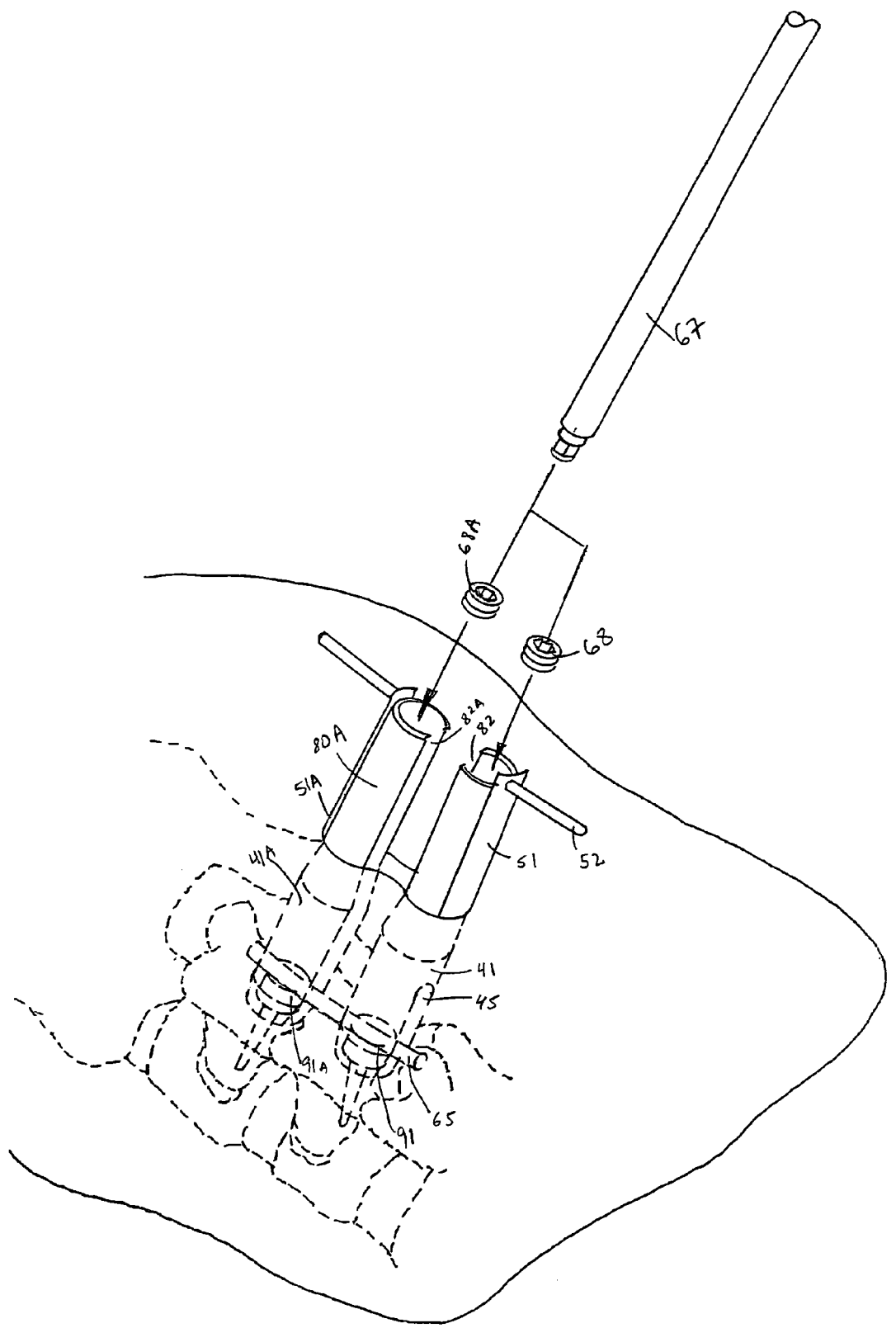
FIG. 13 is a perspective view of the installation of stabilizing rod securement members during a minimally invasive spinal procedure.
Figure 14:
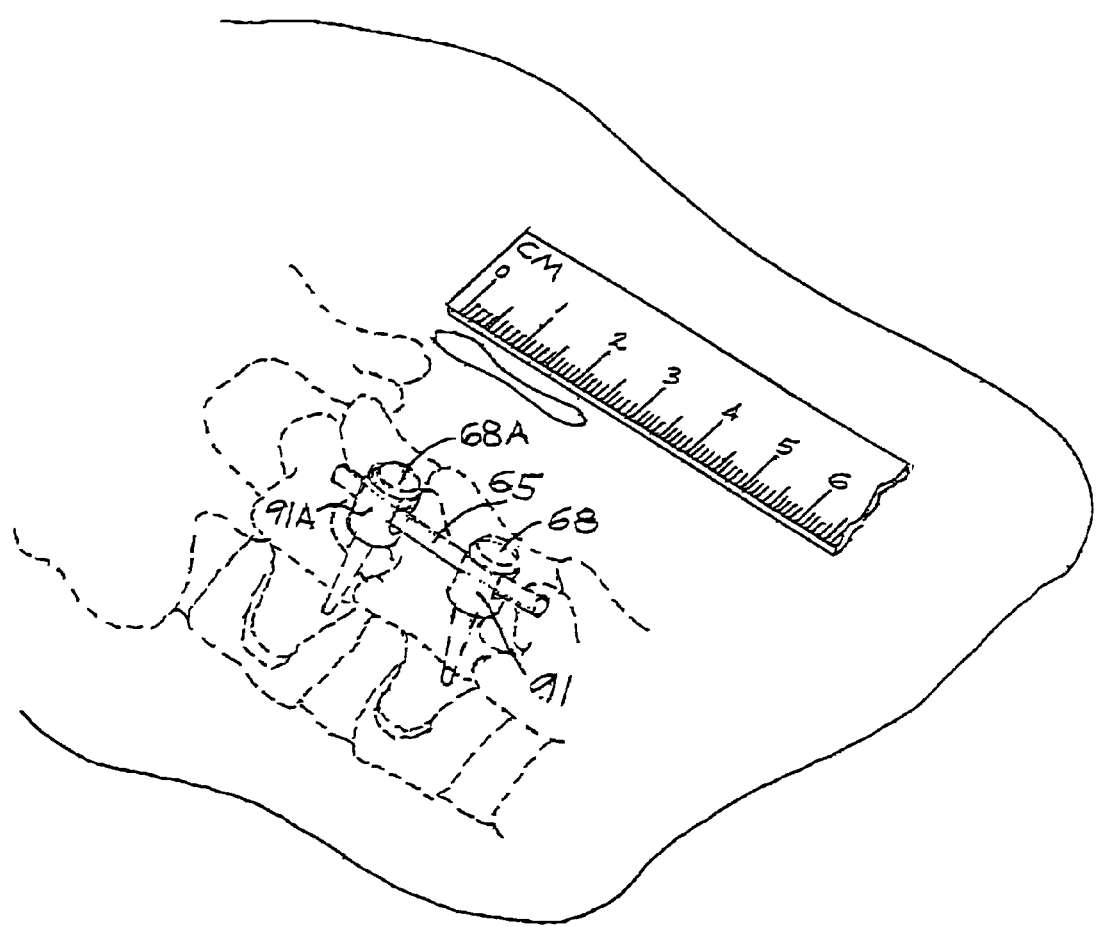
FIG. 14 is a perspective view of the incision after the placement of the stabilization system from a minimally invasive spinal procedure.

Referring then to the drawings wherein the same reference numeral may be used to designate different parts throughout the several views, and referring particularly to FIGS. 15-17, it is seen that the outer sleeve assembly of the present invention includes a lower section 40 preferably having a generally cylindrical wall 41, and an upper extension 51 attached thereto. The upper extension 51 includes an outwardly protruding handle 52 to facilitate easy manipulation, including the installation and removal of the outer sleeve of the invention. The lower section has a longitudinal slot or channel 42 that extends the entire length of the wall 41. Slot 42 is preferably located directly across from extension 51, but may have any other suitable orientation. In the illustrated preferred embodiment, slot 42 gives wall 41 a generally "C" shaped cross section as shown in FIG. 17. Slot 42 corresponds with a similar slot 82 on an inner sleeve 80. Slots 42 and 82 are aligned in order to receive a stabilizing rod 65 as shown in FIG. 12. Stabilizing rod 65 is to be attached to polyaxial screws 90 during surgery, as shown in FIGS. 13-14.

The cross sectional shape of the interior wall 41 of lower section 40 (e.g., the interior diameter 43) is approximately the same as the cross sectional shape of the exterior of inner sleeve 80 (e.g., the outer diameter of sleeve 80), and of the head 91 of screw 90. This allows wall 41 of lower section 40 to slide snugly over the inner sleeve 80 and the screw head 91 coupled to sleeve 80 as shown in FIG. 19. The edges 44 of the wall 41 adjacent to the longitudinal slot 42 may be flattened or otherwise shaped so as to conform to the shape of the corresponding edges 84 of slot 82 of the inner sleeve, and the head 91 of the polyaxial screw 90 where it couples with the inner sleeve 80. Thus, the wall 41 of the outer sleeve can only slide over the inner sleeve 80 and its coupling with screw head 91 if all of these parts are properly oriented. Inner sleeve 80 has two register keys 87a and 87b, that fit snugly into corresponding slots 95a and 95b of screw 90. These keys align slot 94 of the bone screw head with slot 82 of the inner sleeve. (See FIGS. 18 and 19.) This assures a snug fit over the coupling between screw head 91 and inner sleeve 80 to prevent the polyaxial screw 90 from becoming detached from the inner sleeve 80 during surgery. It also assures that the slots 82 and 42 of the inner and outer sleeve, respectively, are properly aligned for receiving a stabilization rod 65.

Register flats 84a.b.c.d. of the inner sleeve 80 (FIG. 18) align with the corresponding register flats 44a.b.c.d. of the outer locking sleeve 40 (lower section—FIG. 19). They consequently align slots, 82 of the inner sleeve, and slot 42 of the outer locking sleeve and provide a guide path for stabilizing rod 65. Furthermore register flats 44a.b.c.d. align and engage with flats on the bone screw (not numbered).

It is this engagement and locking of the outer sleeve to the bone screw in unison with the wall section strength that provides the needed mechanical strength to keep the register keys 87a and 87b of the inner sleeve 80 locked to the bone screw slots 95a and 95b. The strong coupling of inner sleeve 80 to the bone screw is therefore secured by the outer locking sleeve 40 without the use of delicate securing screws and their unreliability.

In one embodiment, wall 41 may be provided with a second longitudinal opening 45 in the form of a partial channel or slot located approximately directly across from the full slot 42, as shown in FIG. 16. The location of partial slot 45 is dictated by the location of the corresponding partial slot 85 in inner sleeve 80. See FIG. 21. In this double slotted embodiment, the second slot 45 allows the stabilization rod 65 to pass through both slots 42 and 45 of wall 41, as well as slots 82 and 85 of sleeve 80, rod 65 extending out from the lower section 40 in approximately opposite directions as shown in FIG. 13. Additional slot 45 also allows rod 65 to be attached to adjacent polyaxial screws 90 during surgery. It is to be appreciated that the orientation of slots 42 and 45 may be varied according to the locations of corresponding slots 82 and 85 of inner sleeve 80.

Figure 8:
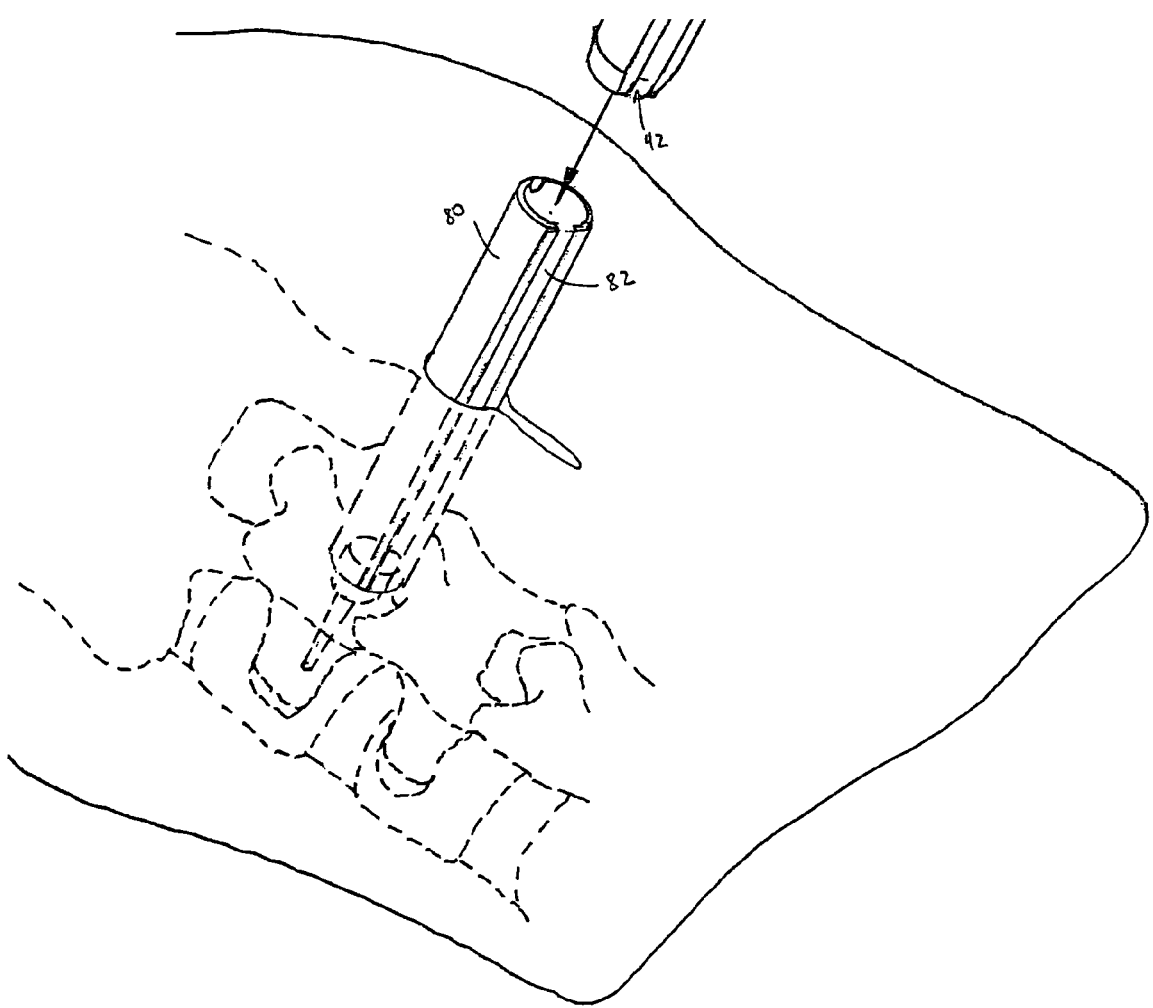
FIG. 8 is a perspective view of the placement of the outer sleeve of the present invention over the inner sleeve of the present invention after the fixation of the screw to the pedicle during a minimally invasive spinal procedure.
Figure 9:
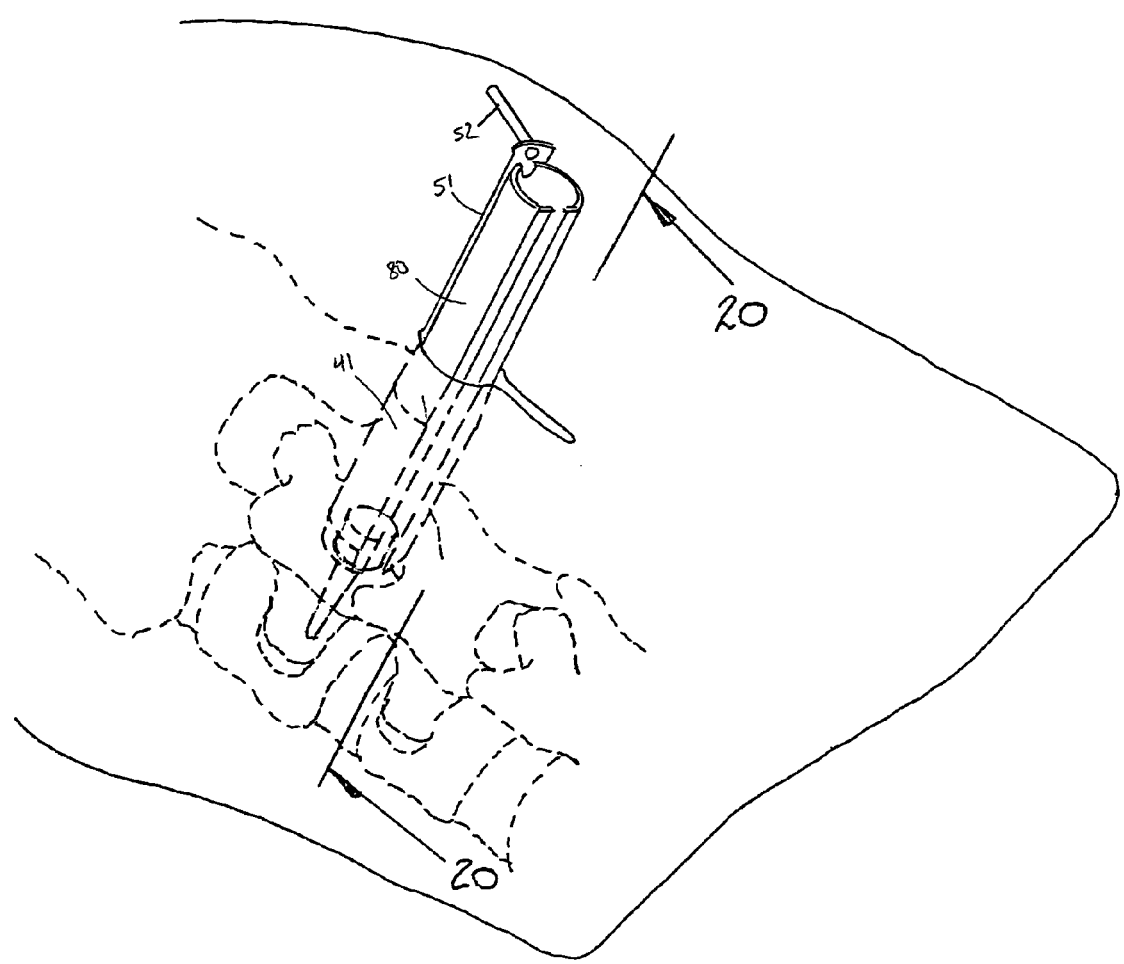
FIG. 9 is a perspective view of the orientation of the inner and outer sleeve assemblies of the present invention during a minimally invasive spinal procedure.
Figure 10:
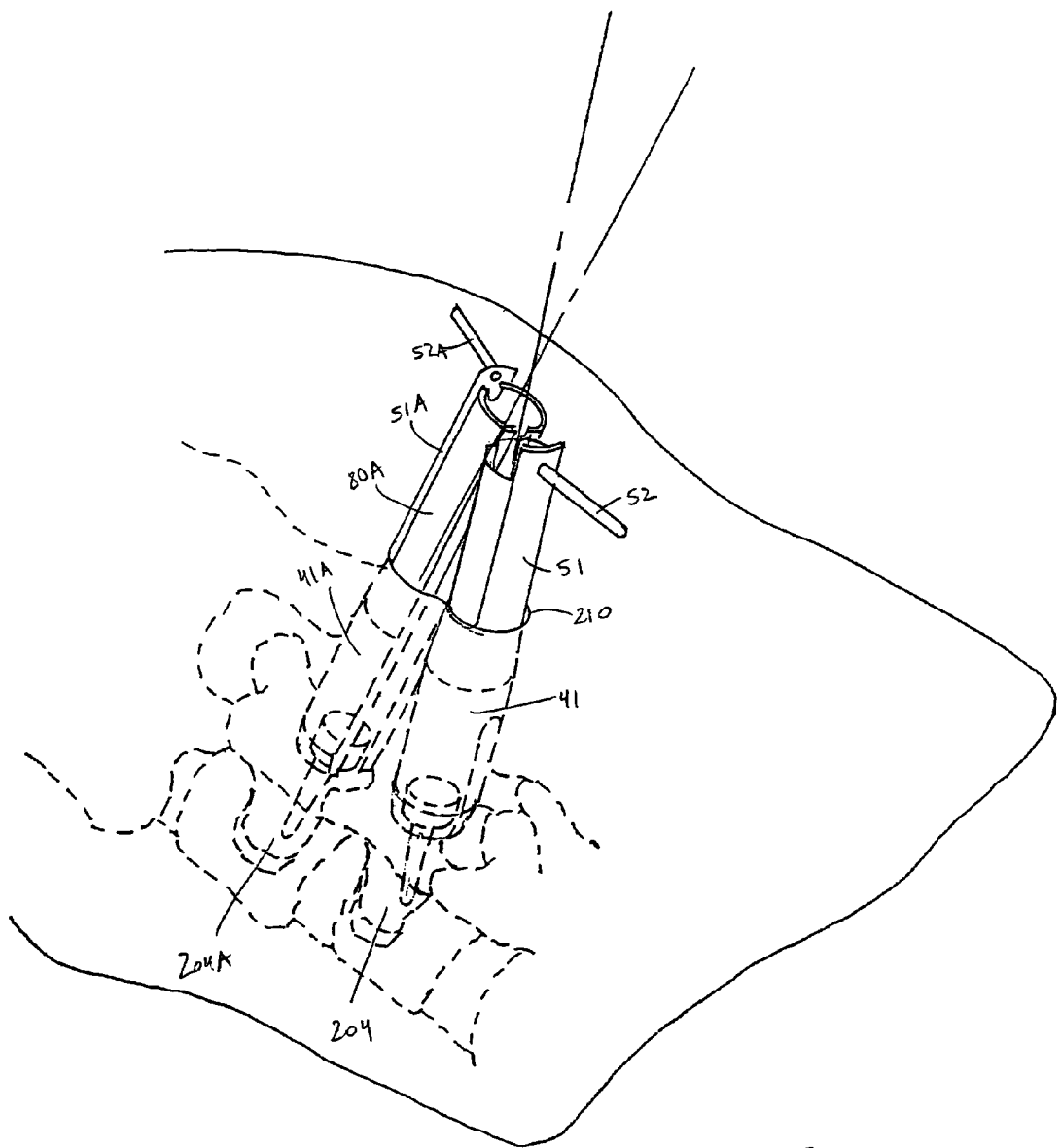
FIG. 10 is a perspective view of the orientation of a pair of inner and outer sleeve assemblies of the present invention as attached to adjacent pedicles during a minimally invasive spinal procedure.

In alternative embodiments, the cylindrical wall 41 of the lower slotted section 40 may be provided with tapered or beveled leading edge 46, and may also be provided with a tapered or beveled trailing edge 47 These tapered edges facilitate easy movement of the generally cylindrical wall 41 through body tissue as it slides around the inner sleeve 80 and the coupling with screw head 91, as shown in FIGS. 8-10.

The upper extension 51 and the handle 52 thereon may be of any suitable length to allow easy access and manipulation of the invention, especially with respect to the insertion and removal of the outer sleeve. The position of handle 52 indicates the location of slots 42 and 82 (and the locations of slots 45 and 85, if present) to the surgeon during surgery.

Minimally invasive procedures are designed to reduce trauma to soft tissue surrounding vertebrae that are to be stabilized. Only a small opening may need to be made in a patient. For example, a single-level stabilization procedure on one side of the spine may be performed through a 2 cm to 4 cm incision formed in the skin of the patient. The incision is generally above and between the vertebrae to be stabilized. Dilators, a targeting needle, and/or a tissue wedge are used to provide access to the vertebrae to be stabilized without the need to form an incision with a scalpel through muscle and other tissue between the vertebrae to be stabilized. Minimally invasive procedures generally reduce the amount of post-operative pain felt by a patient as compared to invasive spinal stabilization procedures, and usually reduce recovery time for the patient.

Figure 1:
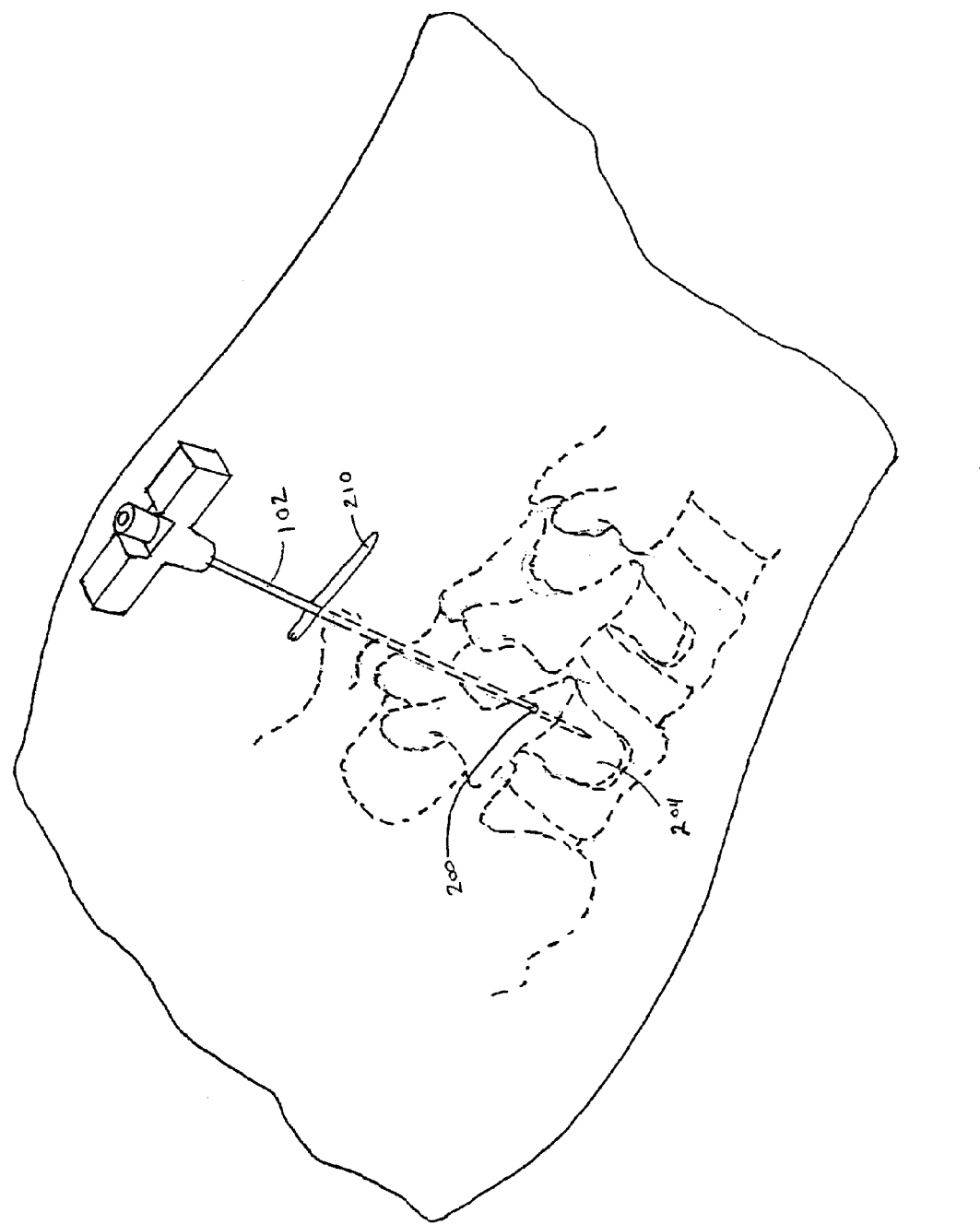
FIG. 1 is a perspective view of positioning the targeting needle to the pedicle during a minimally invasive spinal stabilization procedure.
Figure 2:
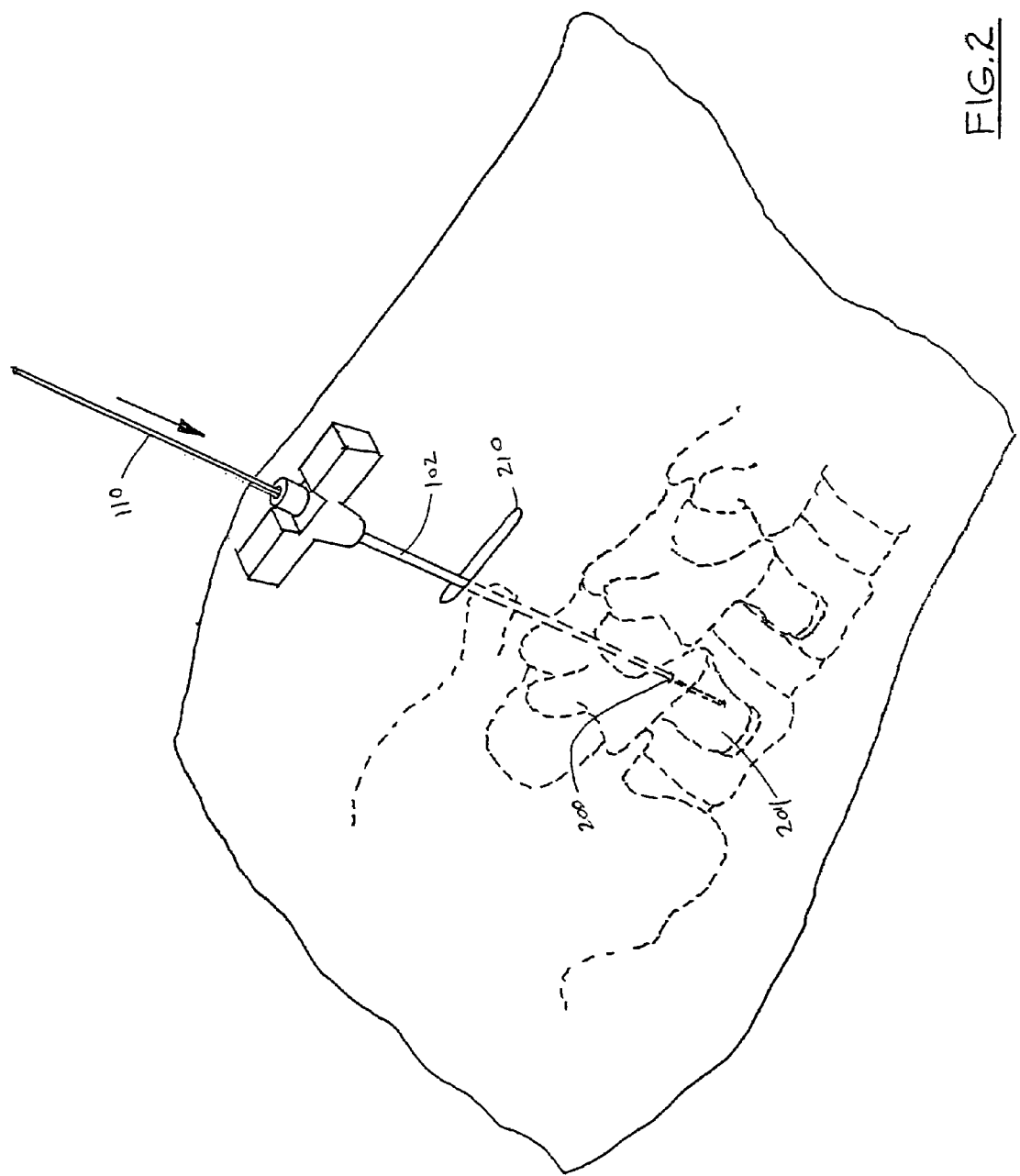
FIG. 2 is a perspective view of guide wire placement to the pedicle during a minimally invasive spinal stabilization procedure.
Figure 3:
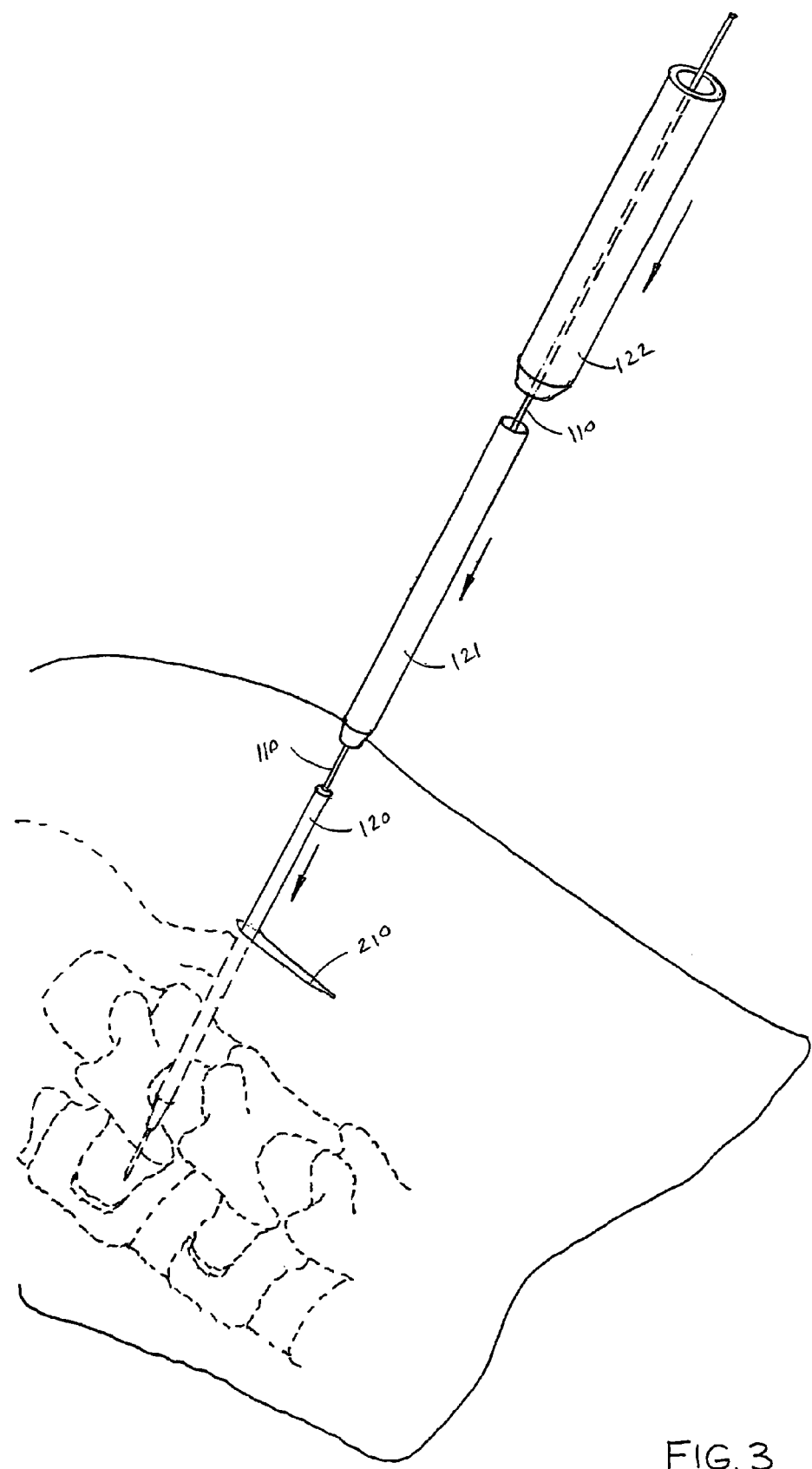
FIG. 3 is a perspective view of the placement of dilators around the guide wire during a minimally invasive spinal stabilization procedure.

Referring to the remaining figures, it is seen that FIG. 1 illustrates a targeting needle 102 advanced to the junction of pedicle 200. FIG. 2 illustrates a guide wire 110 placed through a passage in targeting needle 102 into vertebral body 204. Once the guide wire 110 is secured in body 204, targeting needle 102 may be removed. The guide wire may be used as a guide to position one or more successively sized dilators around a target location in a pedicle to form an opening through soft tissue to the pedicle. FIG. 3 illustrates first, second and third dilators 120, 121 and 122, respectively, positioned around guide wire 110.

Figure 4:
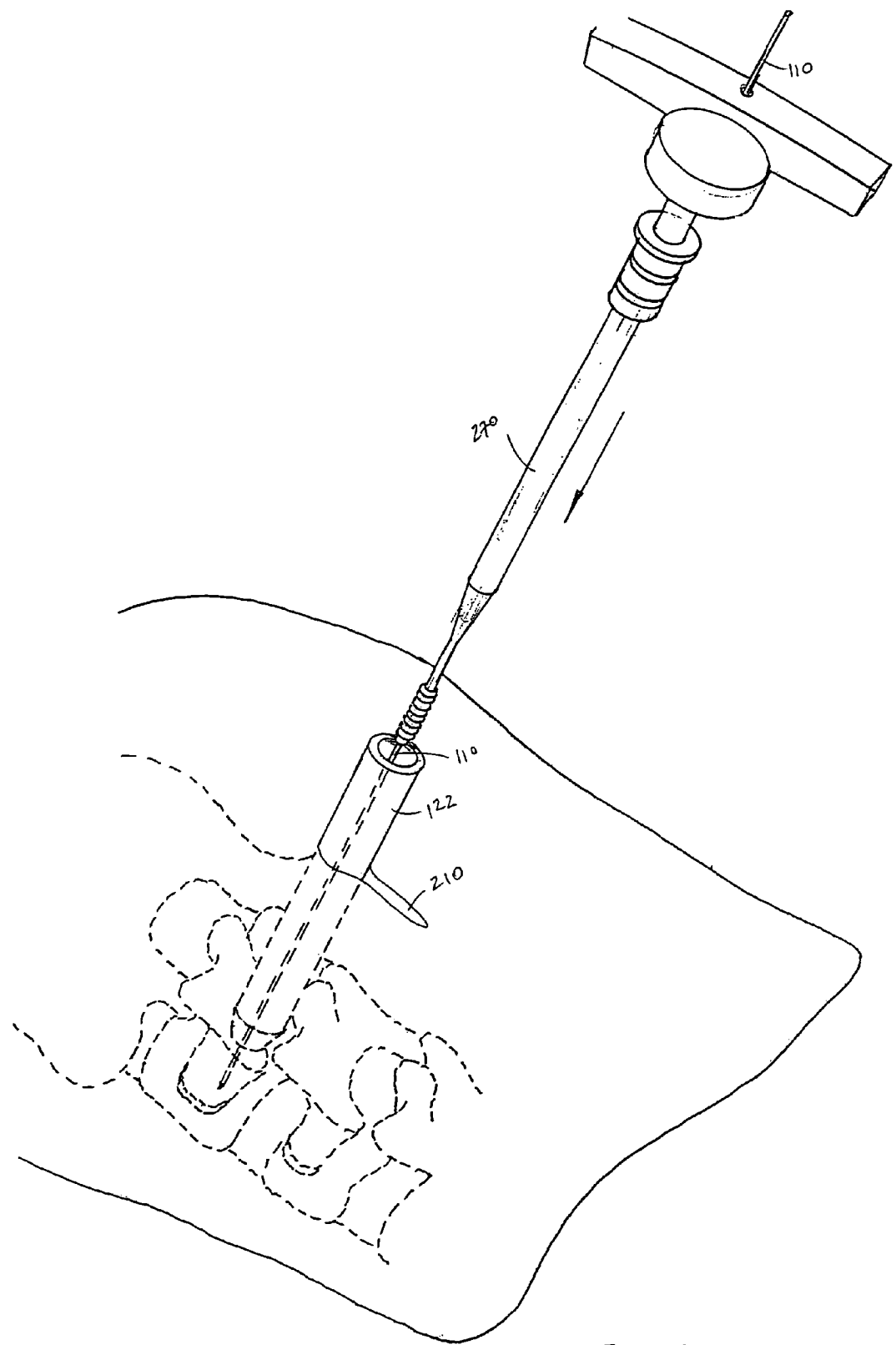
FIG. 4 is a perspective view of the placement of the bone tap on the guide wire before entry of the tap into the dilator and pedicle during a minimally invasive spinal stabilization procedure.
Figure 5:
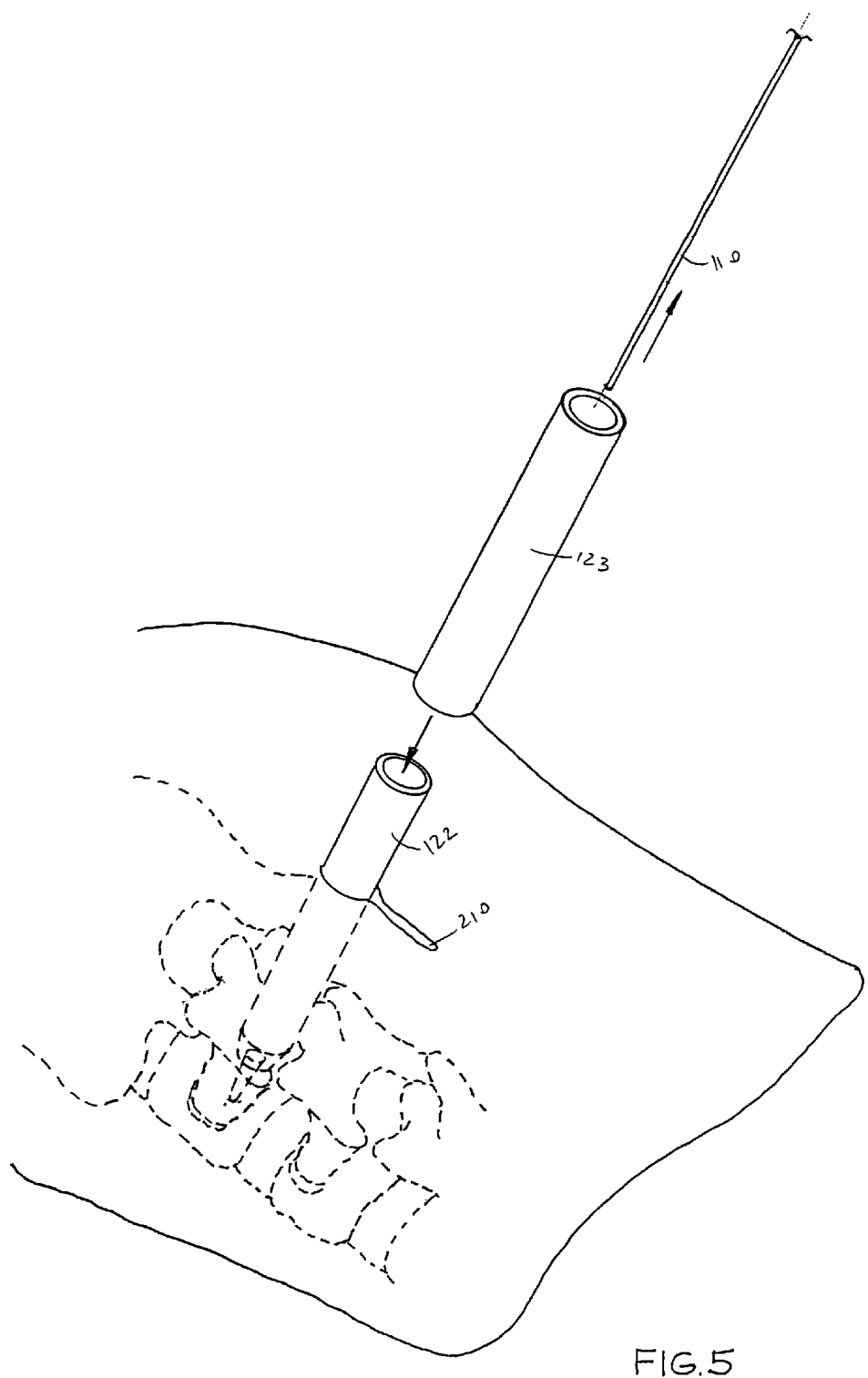
FIG. 5 is a perspective view of the removal of the tap and the placement of a larger dilator over the already inserted dilator during a minimally invasive spinal stabilization procedure.

FIG. 4 shows the third dilator 122 positioned around guide wire 110 following removal of the first dilator 120 and the second dilator 121. This dilator 122 is used to guide a bone screw assembly and/or insertion instruments toward a target location in a pedicle. In FIG. 4, pedicle 200 and vertebral body 204 are prepared for receiving a bone screw assembly using tap 270 inserted over guide wire 110 into dilator 122. Tap 270 is rotated to form a threaded passage through pedicle 200 and into vertebral body 204 to a desired depth. Tap 270 is then removed from vertebral body 204 and pedicle 200 by rotating the tap in the opposite direction out of the vertebral body and the pedicle. The guide wire 110 may then be removed as shown in FIG. 5, or it may be left in place to guide the bone screw assembly 90 to the threaded tap opening.

Figure 6:
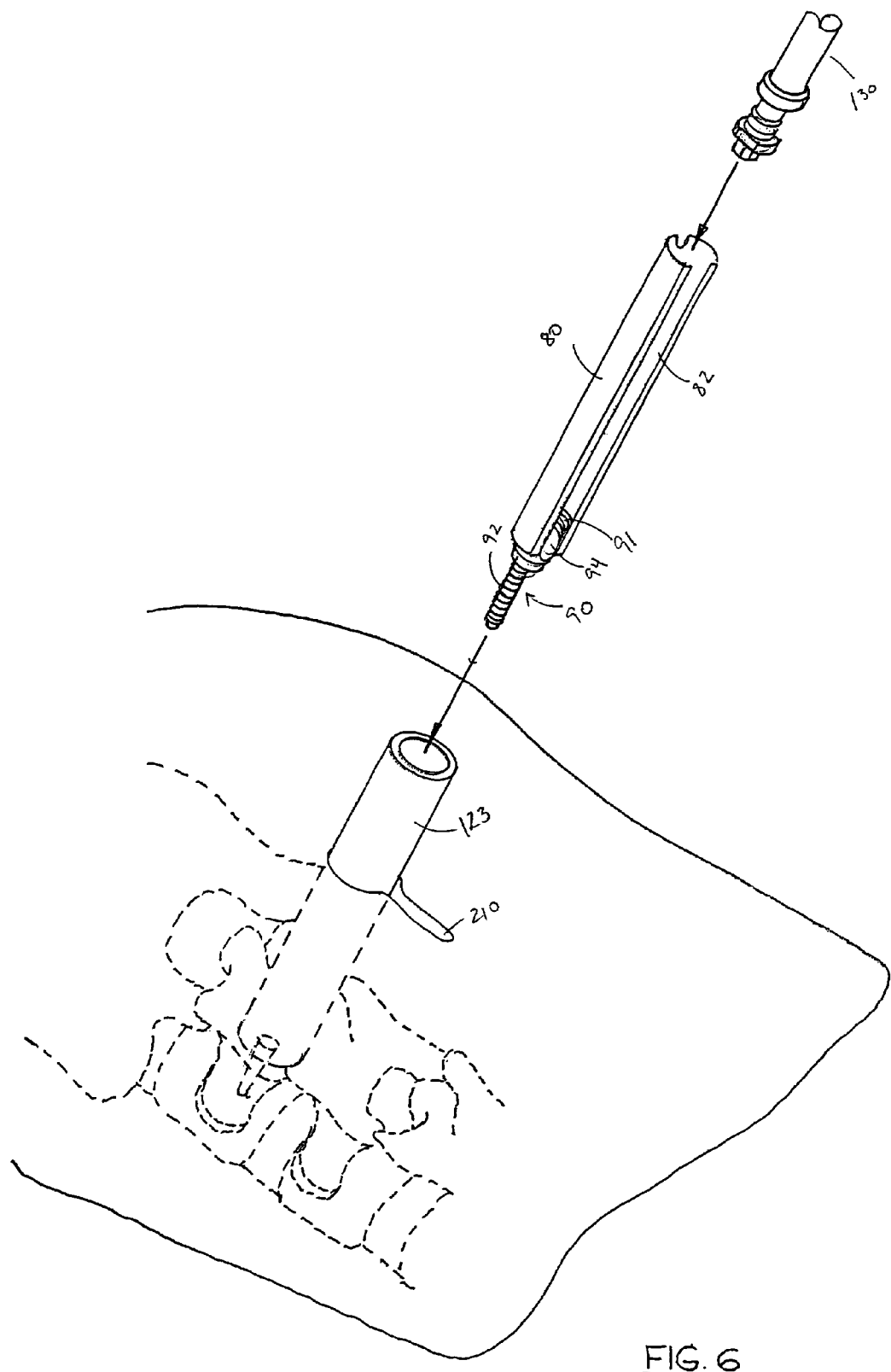
FIG. 6 is a perspective view of the placement of the bone fastener assembly and sleeve assembly in dilator for attachment to pedicle by use of a driver during a minimally invasive spinal procedure.
Figure 7:
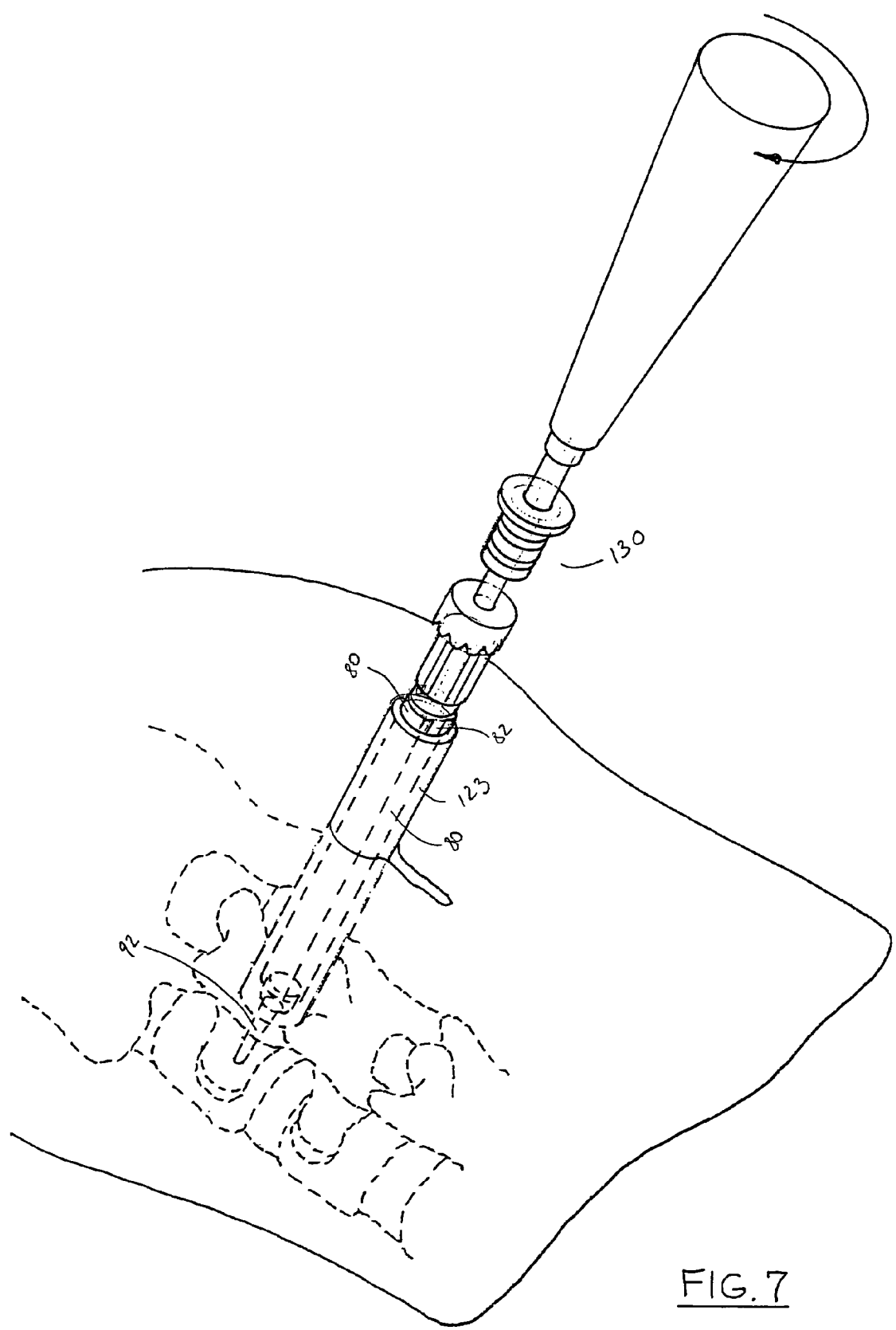
FIG. 7 is a perspective view of the attachment of the bone fastener assembly to pedicle by the clockwise rotation of the driver during a minimally invasive spinal procedure.

An appropriate bone screw assembly 90 is then chosen and attached to the inner sleeve 80, as shown in FIG. 6. The inner sleeve 80, screw head 91, and bone screw 92 are substantially co-axial when inserted into dilator 123, as shown in FIG. 7. A driver 130 is attached to sleeve 80 prior to insertion. After insertion, driver 130 may be rotated to thread the bone screw 90 into pedicle 200 and vertebral body 204. The bone screw 90 is normally advanced to bring the head 91 down snug to the facet joint. FIG. 7 shows the fixation of the bone screw 90 by the clockwise rotation of the driver 130. The bone screw 90 may then be backed off about a quarter of a turn to allow for greater motion of the head 91 relative to the screw portion 92. After the bone screw 90 has been advanced to the desired depth, driver 130 is removed. Dilator 123 may be removed from the patient, as shown in FIG. 8. However, removal of dilator 123 presents the precarious situation of potential detachment of the head 91 of bone screw 90 from sleeve 80.

Promptly after removing dilator 123, the outer sleeve should be oriented and then slidably inserted over inner sleeve 80 all the way down so that lower section 40 slides over the coupling between screw head 91 and sleeve 80. Proper orientation of lower section 40 is quickly and easily achieved using handle 52 on upper extension 51. Once placed over the coupling, the snug fit of lower section 40 prevents detachment of screw head 91 from sleeve 80, as shown in FIG. 9. The polyaxial nature of the screw head 91 allows for angulation of the interior sleeve 80 and the exterior sleeve 40 of the present invention relative to the bone screw 90. Tissue surrounding the incision may be released such that the sleeve is angled toward a central location between vertebrae to be stabilized. The dual sleeve assembly 40, 80 may be moved to facilitate positioning of instruments and/or to facilitate access to the adjacent vertebra that is to be stabilized. For example, the sleeve may be tilted towards the adjacent pedicle so that additional length of an opening in the patient is not needed. The aligned channels 42 and 82 in the sleeves may be turned toward the adjacent pedicle that is to be stabilized, using handle 52.

FIG. 10 shows two inner/outer sleeve assemblies 80/41, and 80A/41A coupled to adjacent vertebral bodies 204/204A. Both sleeve assemblies touch at incision 210 and cross above the body surface, keeping the incision area advantageously small.

With bone screw assemblies secured in the vertebral bodies, the aligned inner and outer sleeves may be oriented to facilitate insertion of an elongated stabilizing rod member 65. The inner and outer sleeves may serve as tissue retractors during a spinal stabilization procedure. The aligned openings in the sleeves may be oriented to face each other, or angled relative to each other in various arrangements.

A distance between the sleeves may be estimated using an estimating tool 141. The distance between the sleeves may be used to select a length of an elongated member needed to couple the collars.

Figure 11:
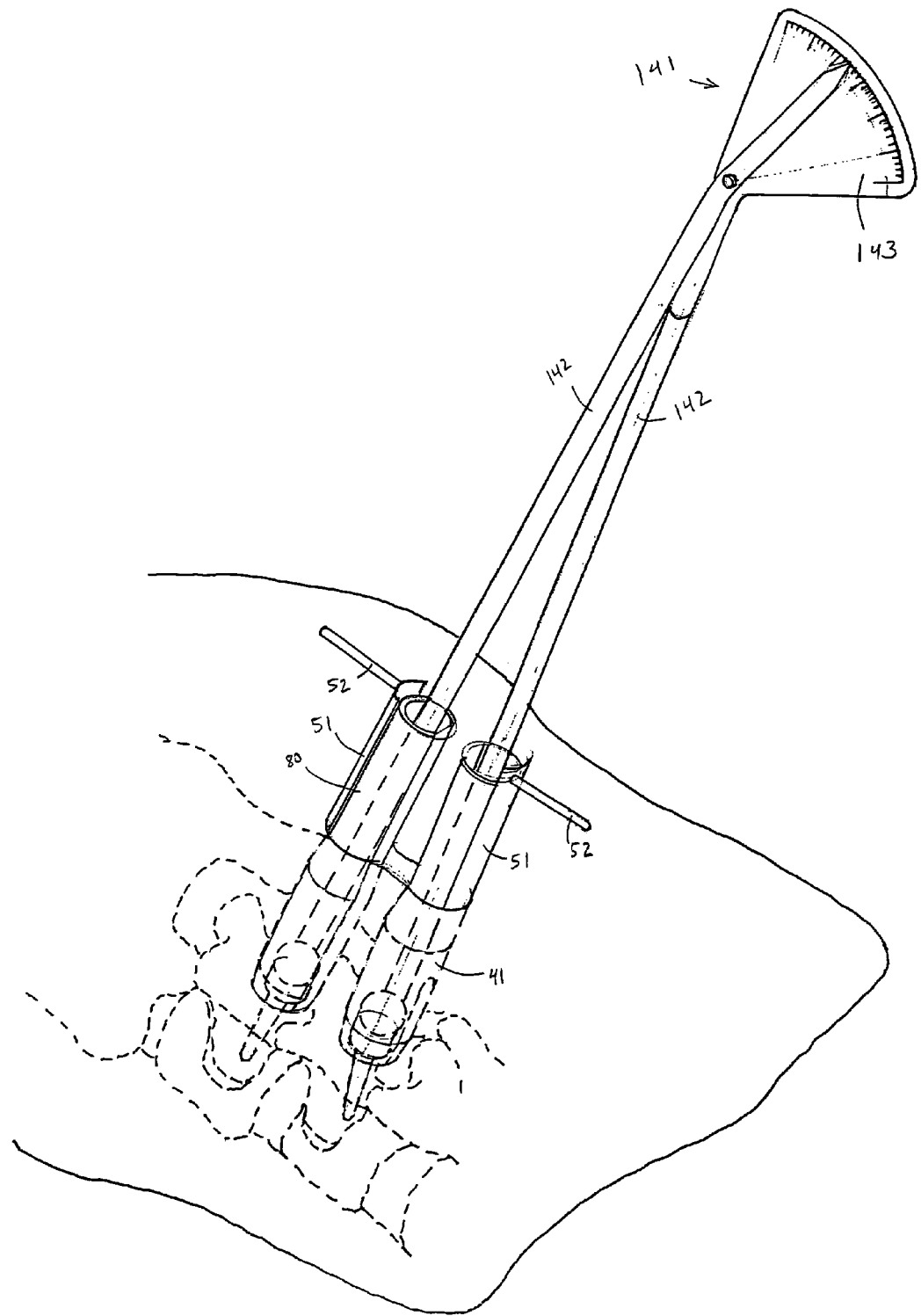
FIG. 11 is a perspective view of the estimating tool as placed in the sleeve assemblies during a minimally invasive spinal procedure.

The arms 142 of estimating tool 141 depicted in FIG. 11 may be positioned in the aligned sleeves and advanced toward the pedicles until the arms of the tool rest on the heads of the bone screw assemblies. At this point, the distance can be measured from the scale 143 at the top of the estimating tool. The length of the stabilizing rod 65 may then be selected based on the distance between the arms 142 of the estimating tool 141. The length of the elongated member may be increased to extend beyond the screw heads after curvature and/or insertion. For example, about 5 mm to about 30 mm (e.g., about 15 mm) may be added to the length of rod 65. Alternatively, the length of the rod 65 may be one that allows the elongated member to extend from each head by about 1 mm, about 2 mm or about 3 mm; or the ends of rod 65 may be made flush with the outer surface of one or more heads.

Rod 65 may also be cut to length and contoured as desired. For example, a medical practitioner may use experience and judgment to determine curvature of a rod 65 for a particular patient or situation. The rod 65 may also be bent or shaped with a tool (e.g., a rod bender) to allow insertion through the aligned channels of the inner and outer sleeves with various spatial locations and/or various angular orientations. Rod 65 may be provided in different shapes including, but not limited to, straight, bent, curved, s-shaped, and z-shaped. Rod 65 preferably has a substantially circular longitudinal cross section; however, it may have other cross-sectional shapes including, but not limited to, regular shapes (oval, rectangular, rhomboidal, square) and irregular shapes. An instrumentation kit for a spinal stabilization system may include straight rods and/or pre-shaped rods. Straight rods and/or pre-shaped rods may be contoured to accommodate patient anatomy if needed during the surgical procedure.

The openings 82 and 85 of inner sleeve 80, as well as the corresponding openings 42 and 45 of the lower sleeve 40 of the present invention may have different orientations to accommodate insertion and seating of differently shaped rods 65. For example, these openings may be non-linear (e.g., bent, curved, or angled) to allow portions of the spine to be selectively stabilized. The sleeve opening orientation and/or design may be chosen to allow compression, distraction, and/or reduction of vertebrae. In some situations, there may be no constraints governing relative location and/or orientation of the upper opening of the sleeve assemblies. The sleeves may be forced apart or angled toward each other or away from each other to accommodate insertion of a rod 65 through the sleeve assemblies for attachment to the bone screw assemblies.

FIG. 12 illustrates insertion of the first end of a rod 65 into the opening or channel 82 of the inner sleeve 80 using a positioning tool 77. As rod 65 is moved along the length of sleeve 80 toward head 91, a second end of the rod 65 may be inserted in the channel 82A of the adjacent sleeve 80A. Slots in the screw heads 91 are aligned with channels 82 and 82A of inner sleeves 80, and with corresponding channels 42 and 42A of the outer sleeves 40 to allow rod 65 to be positioned in the screw heads. Positioning tool 77 may be used to angle the ends of rods 65 so that they protrude from the screw heads through the channels. With one end of rod 65 extending through slot in the first screw head 91, tool 77 may be used to guide the other end of the rod the remaining distance down the second sleeve assembly to second screw head 91A. The shaft of the positioning tool 77 may be curved and/or grooved to allow a rocking motion of rod 65 while it is moved into position. Attachment means 68 are used to affix rod 65 to the screw heads 91 and 91A using a driver 67, as shown in FIG. 13.

After successful attachment, the driver 67 is removed, and sleeves 80 and 80A are ready to be uncoupled from the screw heads 91 and 91A. To accomplish this, the outer sleeves 40 and 40A of the present invention slide off inner sleeves 80 and 80A. This allows uncoupling of the inner sleeves from the screw heads, which can be accomplished with a dislodging motion. Once the outer sleeve is removed from the inner sleeve, a detachment tool is used to momentarily expand the legs of the inner sleeve so as to disengage the register keys of the inner sleeve legs from the bone screw collar allowing the simple retraction of the inner sleeve and the tool at the same time. FIG. 14 illustrates rod 65 attached to screw heads 90 and 91A on adjacent pedicles following removal of the inner and outer sleeves.

Figure 18:
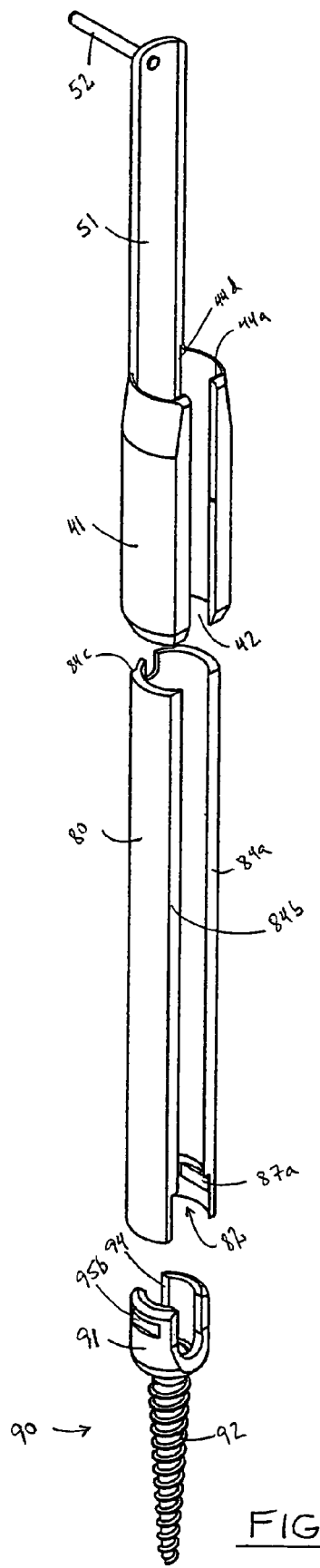
FIG. 18 is an exploded perspective view of an embodiment of the inner and outer sleeves of the present invention, and a bone screw assembly.
Figure 19:
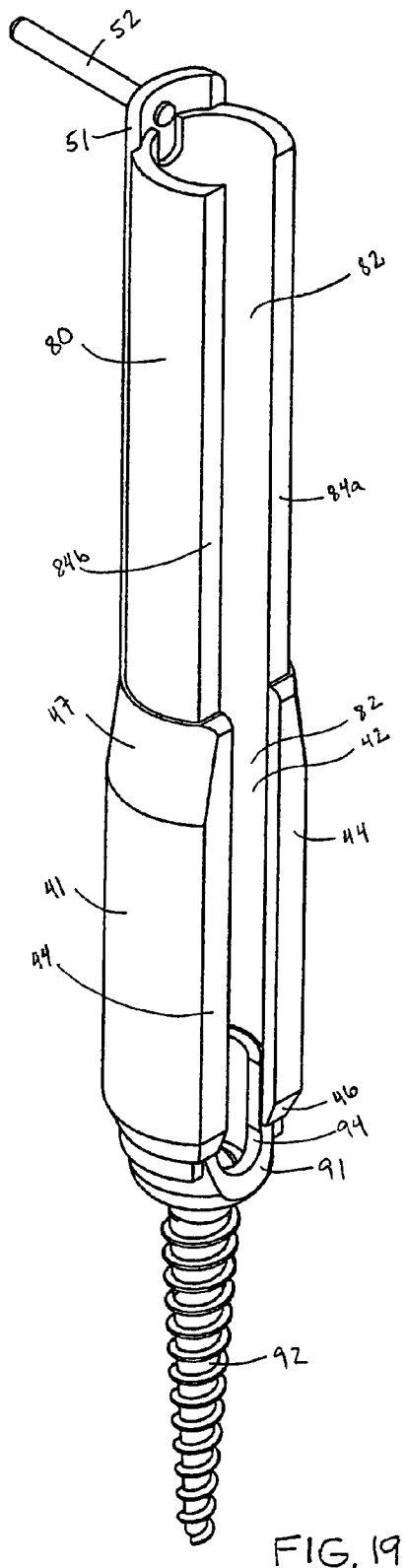
FIG. 19 is a consolidated perspective view of the assemblies of FIG. 18.
Figure 20:
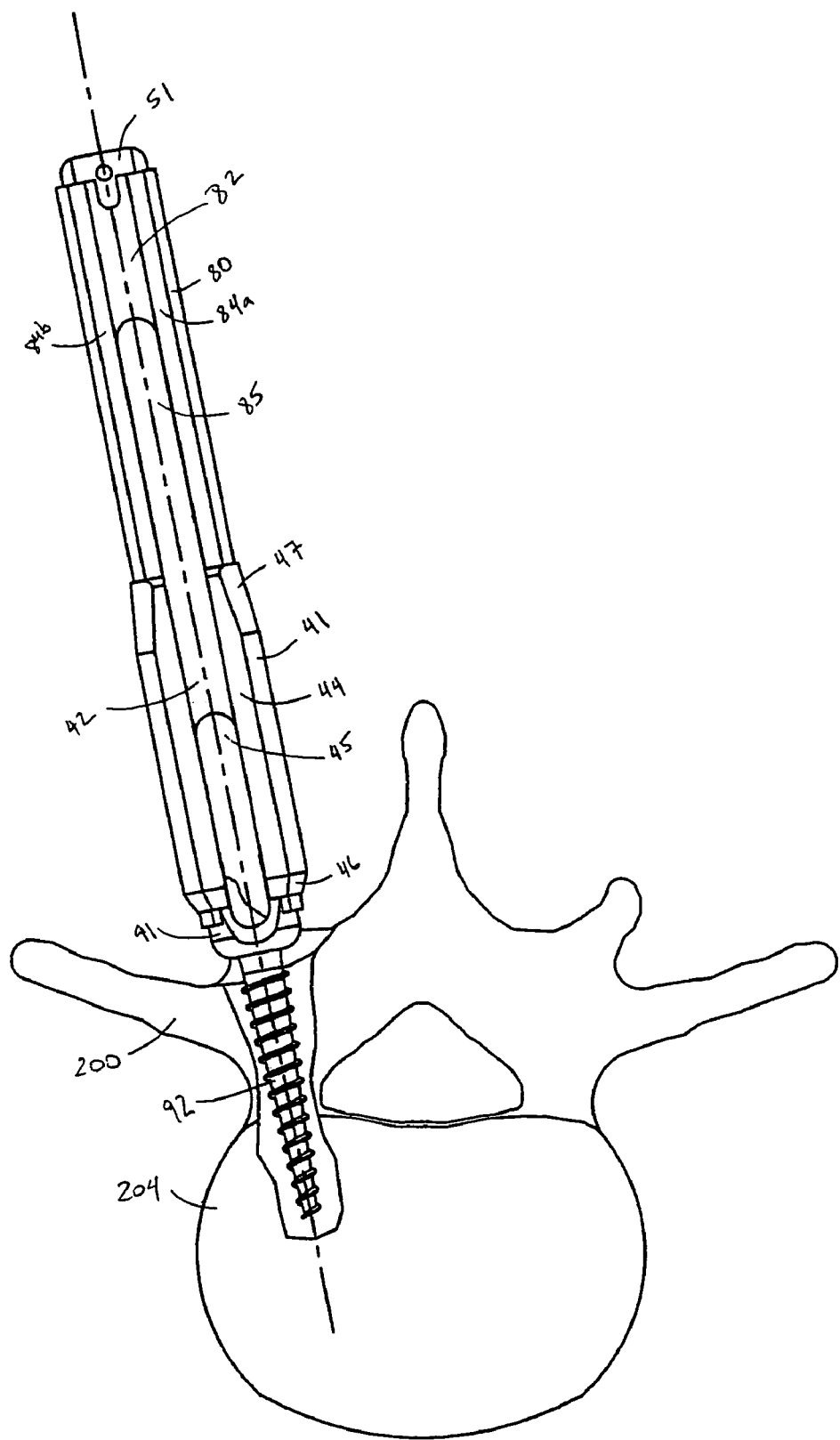
FIG. 20 is a cross sectional view of the consolidated assemblies of FIG. 18 attached to a pedicle and vertebral body during surgery.
Figure 21:
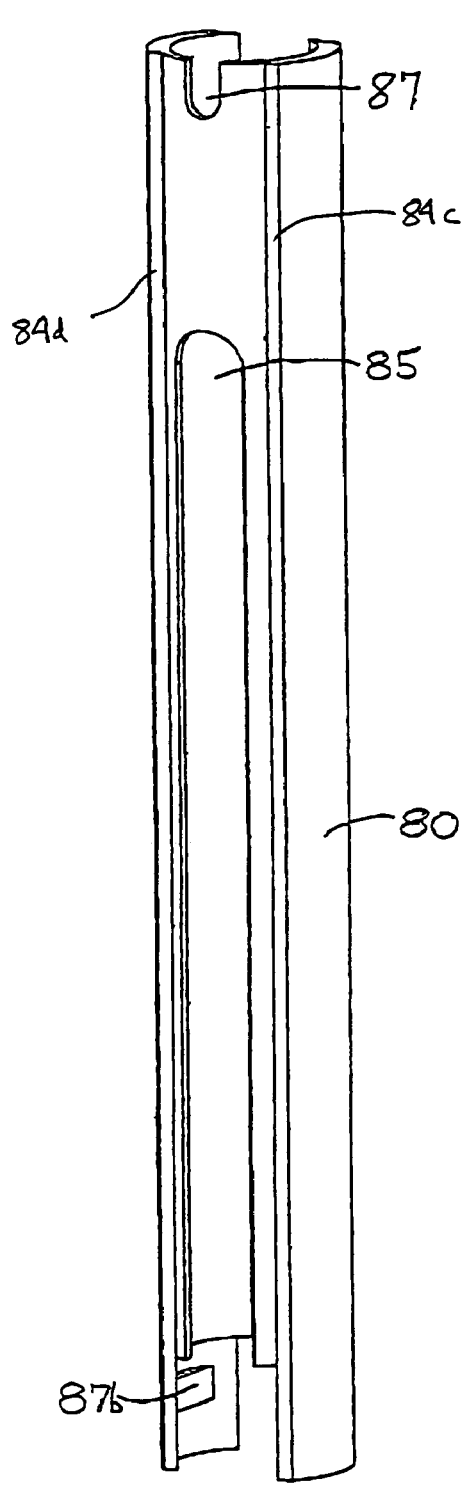
FIG. 21 is a rear perspective view of an embodiment of an inner sleeve of the present invention used in a minimally invasive spinal procedure.
Figure 22:
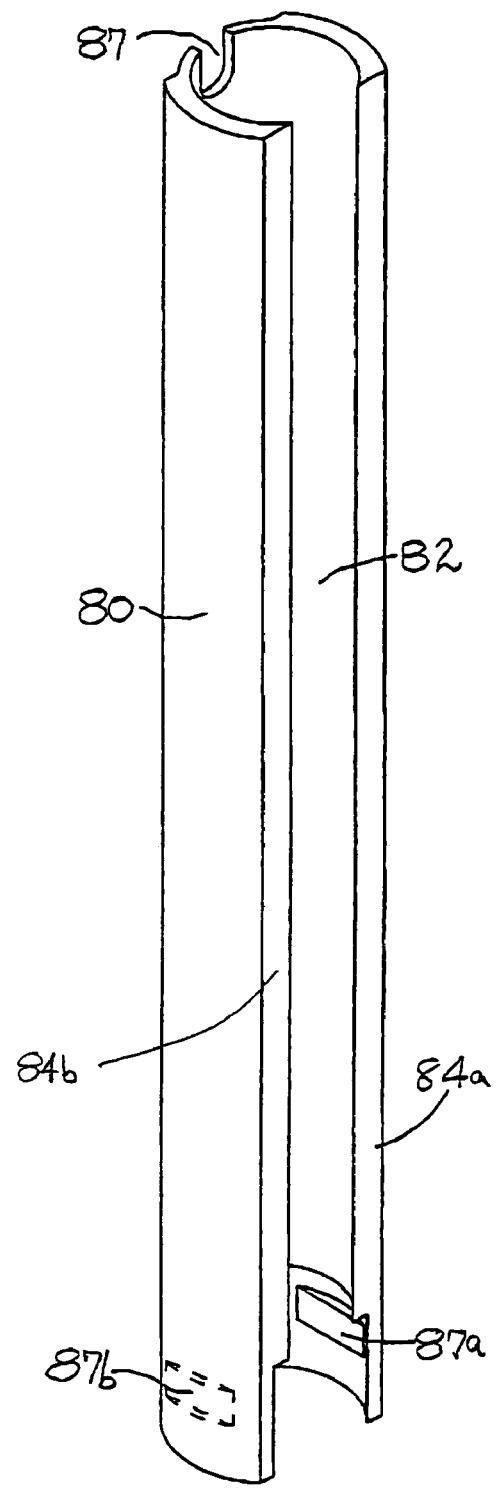
FIG. 22 is a front perspective view of the inner sleeve of FIG. 21.

Mating surfaces are provided on screw heads 91 and inner sleeve 80, For example, as shown in FIGS. 18 and 21, each screw head 91 may be coupled to its corresponding inner sleeve 80 by the insertion of flanges 87a and 87b on each sleeve 80 into corresponding slots 95a and 95b on each screw head 91. This coupling mechanism is less cumbersome to use, and not prone to malfunction or failure. The slots are an essential guide path to securing a stabilizing bar to a slotted bone screw. The secure coupling of a pre-existing poly-axial bone screw to the inner and outer sleeves of the present invention is accomplished in such a way as to not require more than a light finger push to quickly nest the bone screw in the inner sleeve, and an equally fast and light push to rigidly secure the outer sleeve over the already coupled inner sleeve and bone screw. A simple plunger device is supplied for retracting the inner sleeve. It can also be used to nest the bone screw in the inner sleeve. If one were to time the coupling and un-coupling of the inner and outer sleeve system of the present invention to a bone screw using the plunger, it would be expected to take less than 30 seconds FIG. 20 illustrates a cross sectional view of a typical bone screw assembly 90 affixed to a pedicle 200 and vertebral body 204. It should be noted that the head of the bone screw assembly is capable of poly-axial rotation after being fixed. This also allows for poly-axial rotation of inner sleeve 80, and the channel thereon, as well as outer sleeve 40 and the corresponding channels thereon.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention.

It is to be understood that variations and modifications of the present invention may be made without departing from the scope thereof. It is also to be understood that the present invention is not to be limited by the specific embodiments disclosed herein, but only in accordance with the appended claims when read in light of the foregoing specification.

What is claimed is:

1. An assembly for use during minimally invasive spinal stabilization surgery comprising:
    a slotted inner sleeve that couples to a polyaxial screw, the coupling configured to prevent longitudinal motion and rotation of a head of the polyaxial screw with respect to the slotted inner sleeve,
    a slotted outer sleeve that slides over said inner sleeve and a portion of said polyaxial screw to prevent the coupling between said inner sleeve and said polyaxial screw from becoming disengaged during surgery, said outer sleeve comprising a lower section shorter than said inner sleeve, and an upper extension extending from said lower section,
    wherein said lower section is configured for insertion entirely within an incision with only said upper extension and said inner sleeve projecting outside the incision, and
    wherein said lower section includes a tapered trailing edge.

2. The assembly for use during minimally invasive spinal stabilization surgery of claim 1, wherein said upper extension further includes an outwardly protruding handle attached to said extension.

3. The assembly for use during minimally invasive spinal stabilization surgery of claim 1, wherein said inner sleeve has a first longitudinal slot running an entire length of said inner sleeve, and said outer sleeve has a first longitudinal slot running an entire length of said lower section of said outer sleeve, each of said first slots being aligned with each other when the sleeves are engaged.

4. A sleeve assembly for use during minimally invasive spinal stabilization surgery comprising a generally cylindrical inner sleeve assembly having a first longitudinal slot running an entire length of the sleeve, a plurality of register flats extending along the edges of said slot, and a second partial longitudinal slot extending from a bottom edge of the inner sleeve across from said first slot; an outer sleeve assembly having a lower slotted section including a first slot running an entire length of said lower section, a plurality of register flats corresponding to the register flats of said inner sleeve, an upper extension having an outwardly protruding handle thereon, and a second partial slot extending from the bottom edge the lower slotted section across from said first slot; such that the outer sleeve assembly slides over the inner sleeve assembly in an orientation determined by the mating of the register flats of the inner sleeve assembly and the register flats of the outer sleeve assembly to prevent rotation of the inner sleeve assembly with respect to the outer sleeve assembly, the register flats of the outer sleeve assembly engaging a pair of flat surfaces on a head of a polyaxial screw assembly thereby preventing the polyaxial screw assembly from becoming disengaged from the inner sleeve assembly during surgery.

5. The sleeve assembly of claim 4, wherein each of said sleeves has a generally cylindrical cross section, and the interior diameter of the outer sleeve is approximately the same as the exterior diameter of the inner sleeve.

6. The sleeve assembly of claim 5, wherein the cylindrical section of the outer sleeve has a tapered leading edge and a tapered trailing edge.

7. The sleeve assembly of claim 4, wherein said inner sleeve has at least one inwardly-projecting key that corresponds to at least one recessed slot in a head of said polyaxial screw.

8. The assembly for use during minimally invasive spinal stabilization surgery of claim 4, wherein said outer sleeve comprises a lower section having a tapered trailing edge.

9. A method of using a sleeve assembly during minimally invasive spinal surgery comprising:
    a. coupling a slotted inner sleeve to a polyaxial screw assembly, the coupling configured to prevent longitudinal motion and rotation of a head of the polyaxial screw with respect to the slotted inner sleeve;
    b. sliding a slotted outer sleeve over said inner sleeve and a portion of said polyaxial screw to prevent the coupling between said inner sleeve and said polyaxial screw from becoming disengaged during surgery, said outer sleeve comprising a lower section shorter than said inner sleeve, and an upper extension extending from said lower section, wherein said lower section includes a tapered trailing edge;
    c. inserting said lower section entirely within an incision with only said upper extension and said inner sleeve projecting outside the incision.

10. The method of claim 9, wherein said upper extension further includes an outwardly protruding handle attached to said extension.

11. The method of claim 9, wherein said inner sleeve has a first longitudinal slot running an entire length of said inner sleeve, and said outer sleeve has a first longitudinal slot running an entire length of said lower section of said outer sleeve, each of said first slots being aligned with each other when the sleeves are engaged.

12. A method of using a sleeve assembly during minimally invasive spinal surgery comprising:
    a. coupling an inner sleeve assembly to a polyaxial screw assembly, said inner sleeve assembly being generally cylindrical and having a first longitudinal slot running an entire length of the sleeve, a plurality of register flats extending along the edges of said slot, and a second partial longitudinal slot extending from a bottom edge of the inner sleeve across from said first slot;
    b. sliding an outer sleeve assembly over said inner sleeve assembly to maintain the coupling between said screw assembly and said inner sleeve during surgery, said outer sleeve assembly having a lower slotted section including a first slot running an entire length of said lower section, a plurality of register flats corresponding to the register flats of said inner sleeve, an upper extension having an outwardly protruding handle thereon, and a second partial slot extending from the bottom edge the lower slotted section across from said first slot; such that the outer sleeve assembly slides over the inner sleeve assembly in an orientation determined by the mating of the register flats of the inner sleeve assembly and the register flats of the outer sleeve assembly to prevent rotation of the inner sleeve assembly with respect to the outer sleeve assembly;
    c. engaging a pair of flat surfaces on a head of said polyaxial screw assembly with the register flats of the outer sleeve assembly thereby preventing the polyaxial screw assembly from becoming disengaged from the inner sleeve assembly during surgery.

13. The method of claim 12, wherein said outer sleeve slides over said inner sleeve from a proximal end of said inner sleeve.

14. The method of claim 12, wherein said inner sleeve assembly is coupled to said polyaxial screw assembly using a pair of keys on said inner sleeve that engage a pair of recesses in a head of said polyaxial screw assembly to prevent longitudinal motion and rotation of the head of the polyaxial screw assembly with respect to the slotted inner sleeve.

15. The method of claim 12, comprising the additional steps of:
   d. removing the outer sleeve from the inner sleeve; and
   e. disengaging the inner sleeve from the polyaxial screw assembly.

16. The method of claim 15, wherein the outer sleeve is removed from the inner sleeve by sliding the outer sleeve off over a proximal end of the inner sleeve.

17. The method of claim 15, wherein the inner sleeve is disengaged from the polyaxial screw assembly by spreading the inner sleeve to disengage keys on the inner sleeve from recesses in a head of the polyaxial screw assembly.

18. The method of claim 12, comprising the additional steps of:
   d. fastening the polyaxial screw assembly to a vertebral body using force transmitted through said inner sleeve.

19. The method of claim 18, comprising the additional steps of,
   e. repeating steps a-d for a second inner and outer sleeve assembly coupled to a second polyaxial screw assembly;
   f. inserting a reinforcing rod between the two sleeve assemblies such that the reinforcing rod extends into the aligned slots in each of said assemblies; and
   g. affixing the reinforcing rod to the polyaxial screws of the first and second assemblies.

20. The method of claim 19, comprising the additional steps of:
   h. removing the first and second outer sleeves from the first and second inner sleeves; and
   i. disengaging the first and second inner sleeves from the first and second polyaxial screw assemblies.

21. The method of claim 20, wherein the first and second outer sleeves are removed from the first and second inner sleeves by sliding the first and second outer sleeves off over a proximal end of the first and second inner sleeves.

22. The method of claim 20, wherein the first and second inner sleeves are disengaged from the first and second polyaxial screw assemblies by spreading the first and second inner sleeves to disengage the keys on the first and second inner sleeves from the recesses in the heads of the first and second polyaxial screw assemblies.

* * * * *